(12) United States Patent
Zebala

(10) Patent No.: US 11,000,488 B2
(45) Date of Patent: May 11, 2021

(54) TREATING PAIN USING DESMETRAMADOL

(71) Applicant: Syntrix Biosystems, Inc., Auburn, WA (US)

(72) Inventor: John A. Zebala, Auburn, WA (US)

(73) Assignee: Syntrix Biosystems Inc., Auburn, WA (US)

(*) Notice: Subject to any disclaimer, the term of this patent is extended or adjusted under 35 U.S.C. 154(b) by 0 days.

(21) Appl. No.: 16/362,139

(22) Filed: Mar. 22, 2019

(65) Prior Publication Data

US 2020/0297661 A1 Sep. 24, 2020

(51) Int. Cl.
| | | |
|---|---|---|
| *A61K 31/135* | (2006.01) | |
| *A61P 25/04* | (2006.01) | |
| *A61K 9/20* | (2006.01) | |
| *A61K 31/167* | (2006.01) | |
| *A61K 31/192* | (2006.01) | |

(52) U.S. Cl.
CPC .......... *A61K 31/135* (2013.01); *A61K 9/2009* (2013.01); *A61K 9/2013* (2013.01); *A61K 9/2054* (2013.01); *A61K 31/167* (2013.01); *A61K 31/192* (2013.01); *A61P 25/04* (2018.01)

(58) Field of Classification Search
CPC .................................................. A61K 31/135
See application file for complete search history.

(56) References Cited

U.S. PATENT DOCUMENTS

| | | | | | |
|---|---|---|---|---|---|
| 8,324,260 | B1* | 12/2012 | Garcia da Rocha | .... | A61P 25/20 514/396 |
| 9,717,700 | B2* | 8/2017 | Zebala | ................. | A61K 9/2059 |
| 9,717,701 | B2* | 8/2017 | Zebala | ................. | A61K 9/2059 |
| 9,808,432 | B2* | 11/2017 | Zebala | ................. | A61K 31/135 |
| 2013/0011444 | A1* | 1/2013 | Zebala | ................. | A61K 9/2866 424/400 |

OTHER PUBLICATIONS

Guidance for Industry, Bioequivalence Studies with Pharmacokinetic Endpoint for Drugs Submitted Under an ANDA, Dec. 2013.*
NCT03312777, Omnitram Pharmacokinetic and Analgesic Study Following CY2D6 (sic) inhibition with Paroxetine in Healthy Volunteers, ClinicalTrials.gov, Oct. 18, 2017, pp. 1-9.*
"Omnitram Pharmacokinetic and Analgesic Study Following CY2D6 Inhibition With Paroxetine in Healthy Volunteers"; clinicaltrials. gov; NCT03312777; accessed Dec. 9, 2019; 9 pages.
"Omnitram Safety and Effcacy in the Treatment of Diabetic Neuropathy"; clinicaltrials.gov; NCT03664921; accessed Dec. 9, 2019; 9 pages.
International Patent Application No. PCT/US2019/039186; Int'l Search Report and the Written Opinion; dated Jan. 7, 2020; 15 pages.
Bloch et al.; "Tramadol Infusion for Postthoracotomy Pain Relief: A Placebo-Controlled Comparison with Epidural Morphine"; Anesth Analg; vol. 94; 2002; p. 523-528.
Crews et al.; "Clinical Pharmacogenetics Implementation Consortium Guidelines for Cytochrome P450 2D6 Genotype and Codeine Therapy: 2014 Update"; Nature—Clin Pharmacol Ther.; vol. 95 No. 4; Apr. 2014; p. 376-382.
Dart, Richard C.; "The Evolution of the Opioid Abuse Epidemic in North America"; RADARS System In: Lisbon Addictions 2017; Second European Conference on Addictive Behaviors and Dependencies; 17 pages.
De Backer et al.; "Quantification in Postmortem Blood and Identification in Urine of Tramadol and Its Two Main Metabolites in Two Cases of Lethal Tramadol Intoxication"; Journal of Analytical Toxicology; vol. 34; Nov./Dec. 2010; p. 599-204.
Desmeules et al.; "Contribution of monoaminergic modulation to the analgesic effect of tramadol"; Br. J. Clin. Pharmacol; vol. 41; 1996; p. 7-12.
Driessen et al.; "Effects of the central analgesic tramadol on the uptake and release of noradrenaline and dopamine in vitro"; Br. J. Pharmacol; vol. 108; 1993; p. 806-811.
Drug Enforcement Administration. Diversion Control Division. Drug & Chemical Evaluation Section: Tramadol (Trade Names: ULTRAM®, ULTRACET®). Available at: https://www.deadiversion. usdoj.gov/drug_chem_info/tramadol.pdf; Accessed Nov. 5, 2018; Oct. 2018; one page.
Gaedigk et al.; "The CYP2D6 Activity Score: Translating Genotype Information into a Qualitative Measure of Phenotype"; Nature—Clin Pharmacol Ther.; vol. 83 No. 2; Feb. 2008; p. 234-242.
Garrido et al; "Modeling of the In Vivo Antinociceptive Interaction between an Opioid Agonist, (+)-O-Desmethyltramadol, and a Monoamine Reuptake Inhibitor, (−)-O-Desmethyltramadol, in Rats"; The Journal of Pharmacology and Experimental Therapeutics; vol. 295 No. 1; 2000; p. 352-359.
Greenblatt, David J.; "Opioid Prescribing: What Are the Numbers?"; Clinical Pharmacology in Drug Development; vol. 7; 2018; p. 6-8.
Grond et al.; "Clinical Pharmacology of Tramadol"; Clinical Hharmacokinetics; vol. 43 No. 13; 2004; p. 879-923.
Hagelberg et al.;"Ticlopidine inhibits both O-demethylation and renal clearance of tramadol, increasing the exposure to it, but itraconazole has no marked effect on the ticlopidine-tramadol interaction"; Eur J Clin Pharmacol; vol. 69, 2013; p. 867-875.
Houmes et al.; "Efficacy and Safety of Tramadol Versus Morphine for Moderate and Severe Postoperative Pain With Special Regard to Respiratory Depression"; Anesthesia and Analgesia; vol. 74; 1992; p. 510-514.
Janssen Pharmaceuticals I: FDA Labeling.; ULTRAM®—Tramadol hydrochloride tablet; 2017; 45 pages.
Kayser et al.; "Effects of the analgesic agent tramadol in normal and arthritic rats: comparison with the effects of different opioids, including tolerance and cross-tolerance to morphine"; European Journal of Pharmacology; vol. 195; 1991; p. 37-45.
Kayser et al.;"Evidence for a noradrenergic component in the antinociceptive effect of the analgesic agent tramadol in an animal model of clinical pain, the arthritic rat"; European Journal of Pharmacology; vol. 224; 1992; p. 83-88.
Kirchheiner et al.; "Effects of the CYP2D6 Gene Duplication on the Pharmacokinetics and Pharmacodynamics of Tramadol"; Journal of Clinical Psychopharmacology; vol. 28 No. 1; Feb. 2008; p. 78-83.

(Continued)

*Primary Examiner* — Svetlana M Ivanova
(74) *Attorney, Agent, or Firm* — Knudsen Law LLC

(57) ABSTRACT

There is disclosed a method for treating pain, comprising administering an analgesic oral dosage form comprising desmetramadol substantially free of tramadol.

29 Claims, 6 Drawing Sheets

(56) References Cited

OTHER PUBLICATIONS

Kowalczyk et al.; "Sex Differences and Hormonal Influences on Response to Cold Pressor Pain in Humans"; The Journal of Pain; vol. 7 No. 3; Mar. 2006; p. 151-160.

KuKanich et al.; "Pharmacokinetics of tramadol and the metabolite O-desmethyltramadol in dogs"; J. Vet. Pharmacol. Therap.; vol. 27; 2004; p. 239-246.

LLerena et al. "Interethnic variability of CYP2D6 alleles and of predicted and measured metabolic phenotypes across world populations"; Expert Opinion on Drug Metabolism & Toxicology; vol. 10; 2014; p. 1569-1583.

Mildh et al.; "Effects of Tramadol and Meperidine on Respiration, Plasma Catecholamine Concentrations, and Hemodynamics"; Journal of Clinical Anesthesia; vol. 11; 1999. p. 310-316.

Nielsen et al.; "Two separate dose-dependent effects of paroxetine: mydriasis and inhibition of tramadol's O-demethylation via CYP2D6"; Eur. J. Clin. Pharmacol; vol. 66; 2010; p. 655-660.

Orliaguet et al.; A Case of Respiratory Depression in a Child With Ultrarapid CYP2D6 Metabolism After Tramadol; Pediatrics; vol. 135 No. 3; Mar. 2015; p. e753-e755.

Potschka et al.; "Anticonvulsant and proconvulsant effects of tramadol, its enantiomers and its M1 metabolite in the rat kindling model of epilepsy"; British Journal of Pharmacology; vol. 131; 2000; p. 203-212.

Poulsen et al.; "The hypoalgesic effect of tramadol in relation to CYP2D6"; Clinical Pharmacology & Therapeutics; vol. 60 No. 6; Dec. 1996; p. 636-644.

Purdue Pharma LP: FDA Labeling; OXYCONTIN®—Oxycodone hydrochloride tablet, film coated, extended release, 2016; 45 pages.

Raffa et al.; "Mechanistic and functional differentiation of tapentadol and tramadol"; Expert Opinion Pharma.; vol. 13; 2012; p. 1437-1449.

Raffa et al.; "Basic pharmacology relevant to drug abuse assessment: tramadol as example"; Journal of Clinical Pharmacy and Therapeutics; vol. 33; 2008; p. 101-108.

Raffa et al.; "Opioid and Nonopioid Components Independently Contribute to the Mechanism of Action of Tramadol, an 'Atypical' Opioid Analgesic"; The Journal of Pharmacology and Experimental Therapeutics; vol. 260 No. 1; 1992; p. 275-285.

Rani, Shubha; "Bioequivalence: Issues and perspectives"; Indian J. Pharmacol.; vol. 39 No. 5; Oct. 2007; p. 218-225.

Sachdeva et a.; "Tramadol Overdose Requiring Prolonged Opioid Antagonism"; American Journal of Emergency Medicine; vol. 15 No. 2; Mar. 1997; p. 217-218.

Shadnia et al.; "Tramadol intoxicaton: a review of 114 cases"; Human & Experimental Toxicology; vol. 27; 2008; p. 201-205.

Shatin et al.; "Impact of mailed warning to prescriber on the co-prescription of tramadol and antidepressants"; Pharmacoepidemiology and Drug Safety; vol. 14; 2015; p. 149-154.

Stamer et al.; "Concentrations of Tramadol and O-desmethyltramadol Enantiomers in Different CYP2D6 Genotypes"; Clinical Pharmacology & Therapeutics; vol. 82 No. 1; Jul. 2007; p. 41-47.

Stamer et al.; "Impact of CYP2D6 genotype on postoperative tramadol analgesia"; Pain; vol. 105; 2003; p. 231-238.

Subrahmanyam et al.; "Identification of Cytochrome P-450 Isoforms Responsible for CIS-Tramadol Metabolism in Human Liver Microsomes"; Drug Metabolism and Disposition; vol. 29 No. 8; 2001; p. 1146-1155.

Tarkkila et al.; "Comparison of Respiratory Effects of Tramadol and Oxycodone"; Journal of Clinical Anesthesia; vol. 9; 1997; p. 582-585.

Vickers et al.; "Tramadol: pain relief by an opioid without depression of respiration"; Anaesthesia; vol. 47; 1992; p. 291-296.

Wang et al.;"Effect of the CYP2D6*10 C188T polymorphism on postoperative tramadol analgesia in a Chinese population"; Eur J Clin Pharmacol.; vol. 62; 2006; p. 927-931.

World Health Organization. Expert Committee on Drug Dependence 36th Meeting. Tramadol Update Review Report. Agenda Item 6.1; Jun. 2014; 39 pages.

World Health Organization. Expert Committee on Drug Dependence 39th Meeting. Tramadol Pre-Review Report. Agenda Item 5.3; Nov. 2017; 36 pages.

Wu et al.; "Metabolism of the analgesic drug ULTRAM® (tramadol hydrochloride) in humans: API-MS and MS/MS characterization of metabolites"; Xenobiotica; vol. 32 No. 5; 2002; p. 411-425.

Laugesen et al.; "Paroxetine, a cytochrome P450 2D6 inhibitor, diminishes the stereoselective O-demethylation and reduces the hypoalgesic effect of ramadol"; Clinical Pharmacology Therapeutics; vol. 77; 2005; p. 312-323.

\* cited by examiner (+)-tramadol
serotonergic (-)-tramadol
noradrenergic (+)-O-desmethyltramadol
(+)-M1
mu-opioid agonist (-)-O-desmethyltramadol
(-)-M1
noradrenergic

TREATING PAIN USING DESMETRAMADOL

GOVERNMENT RIGHTS

The present disclosure was made with the support of National Institutes of Health grant DA027304. The federal government has certain rights in this invention under 35 USC 200 et seq.

TECHNICAL FIELD

The disclosure herein provides methods for the treatment of pain using desmetramadol.

BACKGROUND

In the United States 25 million people suffer from daily pain. It is common to use a numeric scale to rate pain intensity where '0' equals no pain and '10' is the worst pain imaginable. Pain intensity is broadly categorized as mild (score 4 or less), moderate (score 5 to 6) and severe (score 7 to 10). For example, the acetaminophen for injection 2015 U.S. FDA label states that it is indicated for the "management of mild to moderate pain." Currently, schedule II opioids under the Controlled Substance Act (codified at 21 USC § 801 et seq.) are the mainstay treatment for patients with moderate to severe pain (e.g., codeine, oxycodone, hydrocodone and fentanyl). However, schedule II opioids are highly addictive and can lead to misuse and lethal respiratory depression in an overdose because the same opioid receptor that controls pain transmission also controls the drive to breath. Including opioids like heroin and fentanyl, over 40,000 opioid-related deaths in 2017 in the United States led to what is now known as the Opioid Crisis.

There are unfortunately limited pharmacologic options for patients seeking an alternative to schedule II opioids who still require effective analgesia. A critical unsolved problem therefore exists to identify analgesic options for those suffering from pain that are safer and reduce the risk of treatment-related respiratory depression and death.

Tramadol is approved in the United States for moderate to moderately severe pain, and pain severe enough to require an opioid analgesic (i.e., pain with a score of 5 or greater). The ULTRAM® 2003 United States Food and Drug Administration (FDA)-approved label stated: "ULTRAM is indicated for the management of moderate to moderately severe pain in adults." In 2017, the FDA changed the label with language functionally equivalent to the 2003 label language to read: "ULTRAM is indicated for the management of pain in adults that is severe enough to require an opioid analgesic and for which alternative treatments are inadequate."

As a schedule IV analgesic, tramadol is less prone to abuse than schedule II opioids, and for reasons unrelated to its abuse potential, is safer (Raffa, 2008, *J Clin Pharm Ther,* 33:101-08; Dart, 2017, RADARS SYSTEM, In Lisbon Addictions, Second European Conference on Addictive Behaviors and Dependencies, Lisbon, Portugal; WHO, 2014, Expert Committee on Drug Dependence 36th Meeting, Tramadol Update Review Report, Agenda Item 6.1; WHO, 2017, Expert Committee on Drug Dependence 39th Meeting, Tramadol Pre-Review Report, Agenda Item 5.3). In contrast to schedule II opioids at therapeutic doses, tramadol does not cause clinically significant respiratory depression (Bloch, 2002, *Anesthesia analgesia,* 94:523-28; Grond, 2004, *Clinical pharmacokinetics,* 43:879-923; Houmes, 1992, *Anesthesia analgesia,* 74:510-14; Mildh, 1999, *J clin anesthesia,* 11:310-16; Tarkkila, 1997, *J clin anesthesia,* 9:582-85; Tarkkila, 1998, *Eur J anaesthesiology,* 15:64-68; Vickers, 1992, *Anaesthesia,* 47:291-96). A lethal oral dose of fentanyl, oxycodone and hydrocodone in opioid-naïve and nontolerant subjects can be 2, 40 and 90 mg, respectively (Purdue Pharma LP, 2016, Package Label OXYCONTIN®—Oxycodone hydrochloride tablet, film coated, extended release; U.S. National Library of Medicine: TOXNET. Toxicology Data Network, https://toxnet.nlm.nih.gov). Because a lethal tramadol dose is in excess of 5 grams (De Backer, 2010, *J Analytical Toxicol,* 34:599-604; Sachdeva, 1997, *Amer J Emergency Med,* 15:217-18; Shadnia, 2008, *Human Exp Toxicology,* 27:201-05), reports of lethal overdoses are rare (De Backer 2010; Spiller, 1997, *J Toxicology Clin Toxicology,* 35:361-64).

Tramadol is a racemate consisting of 1R,2R-tramadol [(+)-tramadol], and 1S,2S-tramadol [(−)-tramadol]. After oral administration of the racemate, both the (−) and (+) forms of both tramadol and the 0-desmethyltramadol (M1) metabolite (i.e., both the 1R,2R-isomer and 1S,2S-isomer of O-desmethyltramadol, respectively) are detected in the circulation (Grondhoumer 2004; Raffa, 2012, *Expert Op Pharmacotherapy,* 13:1437-49). The chemical structure and dominant pharmacology of each tramadol and M1 enantiomer are shown in FIGS. 1A-1D. The in vitro µ-opioid receptor binding affinity ($K_i$) is dominated by (+)-M1 (0.0034 µM), compared to substantially weaker affinities for (−)-tramadol (25 µM), (+)-tramadol (1.3 µM) and (−)-M1 (0.24 µM). The in vitro inhibition ($K_i$) of serotonin uptake is dominated by (+)-tramadol (0.5 µM), whereas the inhibition of norepinephrine uptake is mediated by (−)-tramadol (0.5-1.6 µM) and (−)-M1 (0.9-1.4 µM) (Driessen, 1993, *Br J Pharmacol,* 108:806-11; Raffa 2012).

Analgesic activity is a result of binding to µ-opioid receptors, inhibition of reuptake of norepinephrine, and inhibition of reuptake of serotonin (Raffa, 1992, *J Pharmacol Exp Ther,* 260:275-85). The ULTRAM® label states the following.

> The relative contribution of both tramadol and M1 to human analgesia is dependent upon the plasma concentrations of each compound. . . . Opioid activity is due to both low affinity binding of the parent compound and higher affinity binding of the O-demethylated metabolite M1 to µ-opioid receptors. . . . Tramadol-induced analgesia is only partially antagonized by the opiate antagonist naloxone in several animal tests. The relative contribution of both tramadol and M1 to human analgesia is dependent upon the plasma concentrations of each compound. . . . Tramadol has been shown to inhibit reuptake of norepinephrine and serotonin in vitro, as have some other opioid analgesics. These mechanisms may contribute independently to the overall analgesic profile of tramadol.

These statements are also in the ULTRACET® (tramadol plus acetaminophen combination product) label.

Consistent with non-opioid mechanisms of analgesia, tramadol-induced analgesia is only partially antagonized by the opiate antagonist, naloxone, in animals and humans (Raffa 1992; Kayser, 1991, *Eur J Pharmacol,* 195:37-45; Kayser, 1992, *Eur J Pharmacol,* 224:83-88; Collart, 1993, *Br J Clin Pharmacol,* 35:73P). Likewise, in a double-blind, placebo-controlled, crossover study in volunteers, tramadol analgesia was reduced by more than half by an adrenergic receptor antagonist, consistent with tramadol's non-opioid analgesic mechanism involving inhibition of neuronal uptake of norepinephrine (Desmeules, 1996, *Br J Clin Pharmacol,* 41:7-12).

Shortcomings of Tramadol

The FDA recently amended the tramadol label to alert prescribers to the metabolic liabilities that can arise from unsafe M1 levels in patients who are CYP2D6 ultra-rapid metabolizers (Janssen Pharmaceuticals, 2017, Package Label, ULTRAM®—Tramadol hydrochloride tablet; Kirchheiner, 2008, *J Clin Psychopharmacol*, 28:78-83; Orliaguet, 2015, *Pediatrics*, 135:e753-755), and the lack of efficacy that can arise in patients who are metabolically deficient due to either co-prescribed inhibitors of CYP2D6 or suboptimal CYP2D6 genetics (Janssen Pharmaceuticals, 2017; Poulsen, 1996, *Clin Pharmacol Ther*, 60:636-44; Stamer, 2003, *Pain*, 105:231-38; Stamer, 2007, *Clin Pharmacol Ther*, 82:41-47; Wang, 2006, *Eur J Clin Pharmacol*, 62:927-31). The prevalence of the ultra-rapid metabolizer genotype ranges from 4% in Caucasians to 11% in Middle Easterners (LLerena, 2014, *Expert Op Drug Metabol Toxicology*, 10:1569-83). An analysis of over 9,000 prescription claims found tramadol and CYP2D6 inhibitors co-prescribed 21% of the time (Shatin, 2005, *Pharmacoepidem Drug Safety*, 14:149-54). In patients not co-prescribed a CYP2D6 inhibitor, 5-10% carry no functional CYP2D6 alleles and another 2-11% carry one reduced-function and one nonfunctional allele (Crews, 2014, *Clin Pharmacol Ther*, 95:376-82). Abnormal tramadol metabolism is therefore a common occurrence, likely affecting a third to nearly half of patients receiving tramadol. The clinical impact is significant; tramadol was the second most prescribed opioid in the United States with 41 million prescriptions dispensed in 2017 (DEA, 2018, Tramadol, https://www.deadiversion.usdoj.gov/drug_chem_info/tramadol.pdf; Greenblatt, 2018, *Clin Pharmacol Drug Dev*, 7:6-8).

A. Resistance to Tramadol Analgesia

Human tramadol metabolism is extensive and complex. Studies in human liver microsomes and human subjects indicate tramadol is metabolized to M1 by CYP2D6 and to N-desmethyltramadol (M2) by CY2B6 and CYP3A4 (Subrahmanyam, 2001, *Drug Metabol Disposition*, 29:1146-55; Wu, 2002, *Xenobiotica*, 32:411-25). M1 is metabolized to O,N-didesmethyltramadol (M5) by CY2B6 and CYP3A4. Metabolism of tramadol to M1 by CYP2D6 favors the positive enantiomer over the negative enantiomer (Poulsen 1996). Production of M1 in the human can be decreased by either co-administering an inhibitor of CYP2D6, or if a patient's genetics result in a lower than normal amount of CYP2D6 enzyme activity.

Individuals co-administered an inhibitor of CYP2D6 (e.g., paroxetine) exhibited resistance to tramadol analgesia and diminished M1 in their blood (Nielsen, 2010, *Eur J Clin Pharmacol*, 66:655-60; Laugesen, 2005, *Clin Pharmacol Ther*, 77:312-23), as did individuals whose genetics made them CYP2D6 poor metabolizers of tramadol (Kirchheiner 2008).

Using two parallel, randomized, double-blind, placebo-controlled crossover designs, the analgesic effect of tramadol was assessed in 27 volunteers (15 extensive metabolizers 'EMs' and 12 poor metabolizers 'PMs') using several experimental pain models (Poulsen 1996). Differences existed between EMs and PMs that indicated M1 was critical for a portion of the analgesic effect of tramadol (id.).

The effect of CYP2D6 polymorphism on tramadol analgesia was assessed in 300 Caucasian patients undergoing major abdominal surgery (Stamer 2003). Patients who had one or more functional alleles were classified as EMs. Genotyping revealed that 35 patients had no functional alleles and were classified as PMs. Compared to the EMs, the PMs displayed a significantly higher incidence of non-response to tramadol (P=0.005) and required more tramadol or rescue medication (P=0.02).

The effect of CYP2D6 polymorphism (specifically CYP2D6*10, a single nucleotide polymorphism that results in a Pro34 to Ser substitution and reduced CYP2D6 activity) on tramadol-induced analgesia (administered via PCA) was assessed in 63 Chinese patients who underwent gastrectomy for gastric cancer (Wang 2006). The patients were classified as EMs (N=17) or either heterozygous (N=26) or homozygous (n=20) for CYP2D6*10. Compared to the other groups, the homozygous group required more tramadol (P<0.05).

In a study of patients (N=187) undergoing major abdominal surgery reported a 4-fold greater non-response rate to tramadol in CYP2D6 poor metabolizers (Stamer 2007).

In summary, both opioid and non-opioid components of tramadol and its metabolites contribute to its analgesia. The analgesic effect of tramadol is decreased or absent in patients who have low CYP2D6 enzymatic activity because of either their genetics or a co-administered CYP2D6 inhibitor (i.e., a drug-drug interaction).

B. Sensitivity to the Adverse Events of Tramadol

Approximately 2% of northern white European, and 7% of southern Europeans carry the CYP2D6 gene duplication (more than two functional alleles) that results in ultra-rapid metabolism of tramadol, and these ultra-rapid metabolizers (UMs) are more sensitive to the adverse events of tramadol than other genotypes (Kirchheiner 2008). In particular, the pharmacokinetics and effects were monitored after a single dose of 100 mg racemic tramadol in 11 UMs and 11 EMs (i.e. two active alleles). Almost 50% of the UM group experienced nausea compared with only 9% of the EM group.

In rare cases, UMs can experience life-threatening respiratory depression and even death after being administered tramadol (Orliaguet 2015). Due to the risk of respiratory depression and death in CYP2D6 ultra-rapid metabolizers, the FDA amended the labels for ULTRAM® to restrict its use. ULTRAM® is now contraindicated in children younger than 12 years of age and in children younger than 18 years of age following tonsillectomy and/or adenoidectomy.

As described above, among all the enantiomers of tramadol and M1, (+)-tramadol is the most potent inhibitor of serotonin reuptake. The labels for ULTRAM® or ULTRACET® advise using either with great caution in patients taking monoamine oxidase inhibitors or selective serotonin reuptake inhibitors, since their concomitant use increases the risk of adverse events, including seizure and serotonin syndrome. Serotonin syndrome, a potentially fatal adverse drug reaction, involves excess serotonergic activity causing mental status changes, hyperreflexia, fever, shivering, tremor, agitation, diaphoresis, seizures, coma, or death.

M1 Metabolite (O-desmethyltramadol)

M1 has been studied in animals. M1 was administered to female Wistar rats intraperitoneally to analyze adverse events caused by tramadol (Potschka, 2000, *Br J Pharmacol*, 131:203-12) and found not to induce respiratory depression below 10 $mg/kg^{-1}$ and not to cause seizures at 10-30 $mg/kg^{-1}$. M1 was administered to male Sprague-Dawley rats by intravenous infusion to analyze the effect of the in vivo interaction between (+)-M1 and (−)-M1 enantiomers on the antinociceptive effect of tramadol (Garrido, 2000, *J Pharmacol Exp Ther,* 295:352-59). Steady-state plasma concentration levels of 200 ng/ml of (+)-M1 were found to exhibit an antinociceptive response between 50 and 70% of the maximum response, and between the two enantiomers the antinociceptive effect was found potentiated. In another study, tramadol and racemic M1 was administered to beagle dogs, and metabolic stability was measured, including half-life, volume of distribution, and total body clearance (Ku-Kanich, 2004, *J Vet Pharmacol Ther,* 27:239-46). Metabolic stability of tramadol in beagles were found to resemble that in humans.

Zebala US20130011444A1 discloses a human study. O-Desmethyltramadol was orally administered to a normal human subject in different sustained release formulations and a pharmaceutical formulation was derived that replicates the M1 pharmacokinetic profile of M1 produced by administration of immediate release tramadol, ULTRAM®.

SUMMARY

Desmetramadol is the International Nonproprietary Name (INN) for O-desmethyltramadol or M1. As used in the disclosure herein, "desmetramadol" refers to the molecule in a dosage form, and O-desmethyltramadol or M1 are the names used to describe the same molecule in the human body or in bodily fluids (e.g., blood or urine).

Disclosed herein is a method of treatment, comprising administering a pharmaceutical composition of desmetramadol, or a pharmaceutically acceptable salt thereof in an oral dosage form (i. e., a form of desmetramadol suitable for administration) that is substantially free of tramadol, to a human subject suffering from (a) moderate to moderately severe pain, or (b) pain that is severe enough to require an opioid analgesic and for which alternative treatments are inadequate. The dosage form may be for oral or parenteral (e.g., intravenous, subcutaneous, intrathecal) administration.

The method disclosed herein includes treating a subject who is a poor metabolizer of tramadol, an intermediate metabolizer of tramadol, a normal metabolizer of tramadol, or an ultra-rapid metabolizer of tramadol. The method optionally further comprises a step of determining that the subject is a poor metabolizer of tramadol, an intermediate metabolizer of tramadol, a normal metabolizer of tramadol, or an ultra-rapid metabolizer of tramadol, for example by measuring the CYP2D6 genotype of the subject. The method optionally comprises a step of administering an inhibitor of CYP2D6 and/or CYP2B6.

The method disclosed herein includes treating a subject who is a child younger than 12 years of age or a child younger than 18 years of age who has undergone a tonsillectomy and/or adenoidectomy.

The method disclosed herein optionally further comprises a step of administering acetaminophen or ibuprofen, e.g., the pharmaceutical formulation optionally further comprises acetaminophen or ibuprofen.

The method disclosed herein optionally further comprises a step of measuring pain or a change in pain, e.g., wherein the pain is 5 or greater and the change in pain is 0.5 or more, each on a 10 cm visual analog scale or 10-point verbal scale. In one embodiment, the pain being treated is selected from the group consisting of acute pain, chronic pain and neuropathic pain.

The pharmaceutical composition of the method disclosed herein comprises an amount of desmetramadol selected from the group consisting of 10, 20, 30, 40, 50, 60, 70, 80, 90, 100, 110, and 120 mg. In one embodiment of the method, the pharmaceutical composition comprises 10 to 30 mg desmetramadol and is administered every 4-6 hours. In another embodiment, the pharmaceutical composition comprises 30 to 50 mg desmetramadol and is administered every 6-8 hours. In another embodiment, the pharmaceutical composition comprises 40 to 60 mg desmetramadol and is administered every 8-10 hours. In another embodiment, the pharmaceutical composition comprises 60 to 80 mg desmetramadol and is administered every 10-12 hours. In another embodiment, the pharmaceutical composition comprises 80 to 120 mg desmetramadol and is administered every 20-24 hours. In another embodiment, the pharmaceutical composition replicates the mean steady-state plasma profile of (+)-O-desmethyltramadol produced by 50 to 300 mg tramadol dosed at the same frequency. In another embodiment, the pharmaceutical composition is substantially bioequivalent to the plasma profile of (1R,2R)-O-desmethyltramadol following administration of tramadol. In another embodiment of the method, the pharmaceutical composition comprises 10 to 120 mg desmetramadol administered as a parenteral injection (e.g., during and after surgery when a subject is unable to take orally administered medication).

In another aspect of the method disclosed herein, the desmetramadol is (1R,2R)-desmetramadol, (1S,2S)-desmetramadol, or a combination of both (1R,2R)-desmetramadol and (1S,2S)-desmetramadol. In one embodiment, desmetramadol is racemic desmetramadol. In another embodiment, the pharmaceutically acceptable salt is desmetramadol hydrochloride.

In another aspect of the method disclosed herein, the pharmaceutical composition further comprises one or more pharmaceutical excipients selected from the group consisting of polysaccharide, acrylic resin, polyalkylene glycol, polyalkylene oxide, polyvinyl acetate, polyvinylpyrrolidone, protein-derived materials, colloidal silica, and mixtures thereof, wherein the pharmaceutical excipients are 10-95 wt. % of the pharmaceutical composition. In one embodiment, the pharmaceutical composition further comprises one or more pharmaceutical excipients selected from the group consisting of microcrystalline cellulose, salts, and magnesium stearate. In another embodiment, the pharmaceutical composition comprises 5-40 wt. % desmetramadol, or a pharmaceutically acceptable salt thereof. In a preferred embodiment, the polysaccharide consists of polysaccharide gums or cellulose ethers. In another preferred embodiment, the cellulose ether consists of hydroxyalkyl celluloses, carboxyalkyl celluloses, or mixtures thereof. In another preferred embodiment, the cellulose ether consists of hydroxyethyl celluloses, hydroxypropyl celluloses, hydroxypropylmethyl-celluloses, carboxy methylcelluloses, or mixtures thereof another preferred embodiment, the acrylic resin consists of polymers or copolymers of acrylic acid, methacrylic acid, methyl acrylate, methyl methacrylate, or mixtures thereof.

In an embodiment of the method disclosed herein, the pharmaceutical composition has a difference factor (f1) of 0 to 15 or a similarity factor (f2) of 50 to 100 for desmetramadol release in an in vitro dissolution profile, wherein the f1 and f2 reference values are 34% desmetramadol released at 1 hour, 50% desmetramadol released at 2 hours, 62% desmetramadol released at 3 hours, 71% desmetramadol released at 4 hours, 85% desmetramadol released at 6 hours, and 93% desmetramadol released at 8 hours. In a preferred embodiment, the in vitro dissolution is measured using a USP Apparatus I Basket Method at 75 rpm in a buffer. In another preferred embodiment, the buffer has a pH selected from 1.2, 4.5, 6.8 and 7.4.

DETAILED DESCRIPTION

Figure 1A:
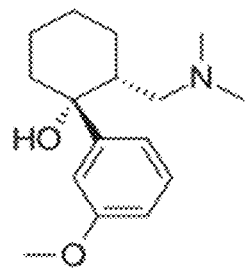
FIGS. 1A-1D shows the chemical structure and dominant pharmacology for (FIG. 1A) (+)-tramadol, (FIG. 1B) (−)-tramadol, (FIG. 1C) (+)-O-desmethyltramadol, also known as (+)-M1, and (FIG. 1D) (−)-O-desmethyltramadol, also known as (−)-M1.
Figure 1B:
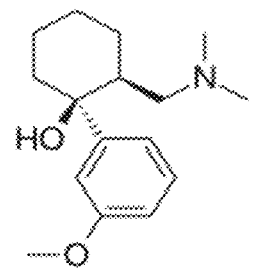
Figure 1C:
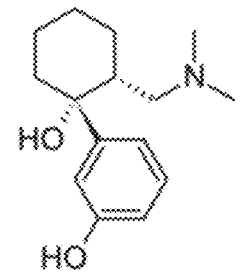
Figure 1D:
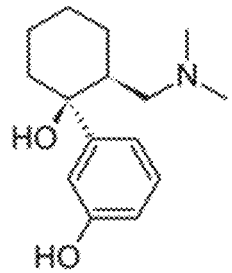

One aspect of the disclosure herein is a method of treating pain, comprising administering to a human subject a pharmaceutical composition comprising desmetramadol in the absence of tramadol, wherein the pharmaceutical composition is safe and effective at providing analgesia equivalent to tramadol to the human subject irrespective of CYP2D6 genotype, that is, even when the human subject is a poor metabolizer, intermediate metabolizer, normal metabolizer or ultra-rapid metabolizer of tramadol, and wherein the human subject requires (a) management of moderate to moderately severe pain, or (b) management of pain that is severe enough to require an opioid analgesic and for which alternative treatments are inadequate.

Another aspect of the disclosure herein is a method of treating pain, comprising administering to a human subject a pharmaceutical composition comprising desmetramadol in the absence of tramadol, wherein the pharmaceutical composition produces a systemic exposure to the M1 enantiomers substantially equal to the systemic exposure of the M1 enantiomers produced by administration of tramadol.

Another aspect of the disclosure herein is a method of treating pain, comprising administering to a human subject every 4-24 hours a pharmaceutical composition of desmetramadol that provides analgesia equivalent to tramadol, wherein the pharmaceutical composition comprises 10 to 120 mg of desmetramadol or a pharmaceutically acceptable salt thereof in a sustained release oral dosage form that is free of tramadol, and is therapeutically effective and safe for a subject who is a poor metabolizer, intermediate metabolizer, normal metabolizer or ultra-rapid metabolizer of tramadol, and wherein the human subject requires (a) management of moderate to moderately severe pain, or (b) management of pain that is severe enough to require an opioid analgesic and for which alternative treatments are inadequate. The method preferably comprises administering 10-20 mg of desmetramadol or a pharmaceutically acceptable salt every 4 hours; or 20-30 mg of desmetramadol or a pharmaceutically acceptable salt every 6 hours; or 30-40 mg of desmetramadol or a pharmaceutically acceptable salt every 8 hours; or 40-60 mg of desmetramadol or a pharmaceutically acceptable salt every 12 hours; or 60-120 mg of tramadol every 24 hours.

The method and composition disclosed herein are the result of the surprising and unexpected discovery that, contrary to thinking in the art, equivalent analgesia to tramadol can be obtained from substantially equal systemic exposure to M1 alone. Tramadol enantiomers, which the art teaches to be pharmacologically active in providing analgesia, are surprisingly and unexpectedly discovered to be unnecessary for desmetramadol alone to provide the same degree of pain relief as tramadol itself. Whereas tramadol is known to lose its efficacy in subjects with depressed CYP2D6 activity, the instant method and composition are also the result of the surprising and unexpected discovery that not only does desmetramadol alone provide pain relief to the same degree as tramadol, but unlike tramadol, its efficacy is immune to depressed CYP2D6 activity and its safety is immune to hyperactive CYP2D6 activity. Thus, desmetramadol alone is unexpectedly discovered to be a safe and effective substitute for tramadol in its approved indications: (a) for the management of moderate to moderately severe pain in adults, and (b) for the management of pain in adults that is severe enough to require an opioid analgesic and for which alternative treatments are inadequate. Because the safety of desmetramadol is immune to the hyperactive CYP2D6 activity in ultra-rapid metabolizers, desmetramadol alone was unexpectedly discovered to be safe and effective for treating pain where tramadol is now contraindicated (i.e., in children younger than 12 years of age and in children younger than 18 years of age following tonsillectomy and/or adenoidectomy).

In order to optimally deliver a substantially equal systemic exposure of M1 as that arising from tramadol metabolism in extensive and intermediate metabolizers, a pharmaceutical composition is required comprising a sustained release dosage form having the same dissolution profile as the reference dissolution profile provided herein. The reference dissolution profile provided herein is critical for providing the pharmaceutical composition with bioequivalence to tramadol (e.g., ULTRAM® IR) with respect to the steady-state maximum ($Css_{max}$) and minimum ($Css_{min}$) plasma concentration of (+)-O-desmethyltramadol. There is said to be 'bioequivalence' between the pharmaceutical composition and tramadol with respect to plasma (+)-O-desmethyltramadol when the 90% confidence interval (CI) of the pharmaceutical composition-to-tramadol Css ratio ($Css_{min}$ or $Css_{min}$ ratio) for a subject population is from 0.8 to 1.25 inclusive (i.e., ≥0.8 and ≤1.25), wherein the ratio is determined using the log-transformed Css value. Calculating bioequivalence according to the 90% CI is well known to those in the art (see, e.g., Rani, 2007, *Indian J Pharmacol*, 39:218-25). Bioequivalence is a critical property for regulatory and therapeutic purposes.

Thus, the present disclosure provides a pharmaceutical composition comprising a sustained release dosage form containing a pharmaceutically effective amount of an desmetramadol, or a pharmaceutically acceptable salt thereof, wherein the in vitro dissolution profile of desmetramadol from the pharmaceutical composition has a difference factor (f1) of 0 to 15, or a similarity factor (f2) of 50 to 100, when compared to the reference dissolution profile provided herein.

The reference dissolution profile for a pharmaceutical composition is 34% desmetramadol released at 1 hour, 50% desmetramadol released at 2 hour, 62% desmetramadol released at 3 hour, 71% desmetramadol released at 4 hour, 85% desmetramadol released at 6 hour, and 93% desmetramadol released at 8 hour.

The method of treating pain comprises administering a pharmaceutical formulation comprising desmetramadol substantially free of tramadol, wherein the method overcomes resistance to tramadol analgesia or sensitivity to tramadol adverse effects caused by genetic or drug-drug metabolic defects. The method further eliminates serotonin reuptake activity caused by tramadol, and thereby reduces the risk of seizure and serotonin syndrome. The method is effective for relieving a disorder modulated by opiate receptor activity and/or monoamine activity, and in particular for relieving acute, chronic and neuropathic pain.

The method disclosed herein includes the additional step of administering a second pharmaceutical composition comprising an analgesic in an immediate-release or sustained release form, for example, an analgesic selected from the group consisting of acetaminophen, aspirin, ibuprofen, diclofenac, naproxen, indomethacin, fenoprofen, oxycodone, nalbuphine, hydromorphone, codeine, hydrocodone and topiramate. A preferred additional active ingredient is a therapeutically effective amount of acetaminophen or ibuprofen. Preferably, the second pharmaceutical composition comprises 300 mg to 700 mg acetaminophen or 150 mg to 600 mg ibuprofen, with 200 mg or 400 mg ibuprofen preferred.

The present disclosure further provides a method for treating disorders modulated by opiate receptor activity or monoamine activity including acute pain, chronic pain and neuropathic pain, comprising orally administering to a human in need thereof the pharmaceutical composition containing a therapeutically effective amount of desmetramadol, or a pharmaceutically acceptable salt thereof, and optionally a therapeutically effective amount of an additional analgesic that is not tramadol (i.e., without concurrently administering tramadol). Preferred optional additional analgesics are ibuprofen and acetaminophen.

The disclosure herein provides an oral pharmaceutical composition consisting solely of the M1 metabolite of tramadol (i.e., desmetramadol) as the active ingredient, and optionally other analgesics (e.g., acetaminophen), that provides a systemic exposure to M1 substantially equal to the systemic exposure of M1 arising from tramadol metabolism in extensive (normal) and intermediate CYP2D6 metabolizers (defined in Genelex Scheme 2, below). This composition is the result of the surprising and unexpected discovery that, contrary to thinking in the art, equivalent analgesia to tramadol can be obtained from substantially equal systemic exposure to M1 alone. In other words, the parent tramadol enantiomers, which the art teaches to be pharmacologically active in providing analgesia, are surprisingly and unexpectedly discovered to be unnecessary for desmetramadol alone to provide the same degree of pain relief as tramadol itself. In order to deliver a substantially equal systemic exposure of M1 as that arising from tramadol metabolism in intermediate and normal metabolizers, an oral pharmaceutical composition is preferably required with the same reference dissolution profile as described herein. Using this pharmaceutical composition, resistance to tramadol analgesia and sensitivity to tramadol adverse effects caused by genetic or drug-drug metabolic defects is overcome. Furthermore, dispensing with the parent tramadol enantiomers, serotonin reuptake activity is substantially eliminated, which may reduce the risk of adverse events such as seizure and serotonin syndrome.

In some embodiments the method of treating pain disclosed herein provides the step of measuring pain before administering desmetramadol and measuring pain after administering desmetramadol. In preferred embodiments pain is measured using a 10 cm visual analog scale (VAS). In other embodiments pain is measured by a subject rating their pain (verbally, writing or pointing) on a verbal, written or visual point scale, e.g., 1 to 5, or 1 to 10 points. In other embodiments pain a measured by asking the patient to report how the pain interferes with their daily life. In some embodiments the method provides the additional step of measuring pain relief, wherein the magnitude of subject-reported pain relief after desmetramadol administration is at least 0.5 points, at least 0.6 points, at least 0.7 points, at least 0.8 points, at least 0.9 points, and most preferably is at least 1.0 points, on a 10 cm VAS or 10-point scale.

In other embodiments the method provides that the desmetramadol is administered together with an inhibitor of CYP2D6 and/or CYP2B6. In this step, the term "administered together" means the inhibitor of CYP2D6 and/or CYP2B6 is taken either before, concurrently with, or after the desmetramadol such that the inhibitor inhibits CYP2D6 and/or CYP2B6. In other embodiments the method provides the additional optional step of measuring the patient's CYP2D6 diplotype (i.e., genotype) either before or after administering the desmetramadol.

A. CYP2D6 Genotype and Metabolizer Phenotype

Most clinical laboratories report CYP2D6 genotype using the star (*) allele nomenclature and may provide interpretation of the patient's predicted metabolizer phenotype (Crews 2014). Single-nucleotide polymorphisms (SNPs) and other sequence variations, including insertions and deletions, are determined by genetic laboratory tests. The reference SNP number (rs number) for a SNP defines the specific genomic nucleotide alteration. Each star (*) allele (or haplotype) is defined by the presence of a specific combination of SNPs and/or other sequence alterations within the CYP2D6 gene locus. Examples of commonly tested polymorphisms defining CYP2D6 variant alleles and their effect on the CYP2D6 protein are shown in Table 1.

TABLE 1

| Allele[a] | Major Nucleotide Variation | dbSNP Number | Effect on CYP2D6 Protein |
|---|---|---|---|
| *1 | — | — | — |
| *1xN | Gene duplication or multiplication | — | Increased protein expression |
| *2[f] | 2850C > T, 4180G > C | rs16947, rs1135840 | R296C, S486T |
| *2xN | Gene duplication or multiplication | — | Increased protein expression |
| *3 | 2549delA | rs35742686 | Frameshift |
| *4 | 100C > T, 1846G > A [4180G > C] | rs1065852, rs3892097 rs1135840 | P34S, splicing defect [S486T] |
| *4xN | Gene duplication or multiplication | — | P34S, splicing defect |
| *5 | Gene deletion | N/A | Gene deletion |
| *6 | 1707delT | rs5030655 | Frameshift |
| *10 | 100C > T, 4180G > C | rs1065852, rs1135840 | P34S, S486T |
| *17 | 1023C > T, 2850C > T, 4180G > C | rs28371706, rs16947, rs1135840 | T107I, R296C, S486T |
| *41 | 2850C > T, 2988G > A, 4180G > C | rs16947, rs28371725, rs1135840 | R296C, Splicing defect, S486T |

[a]*1 is defined as wild-type. See https://www.pharmvar.org for nomenclature updates.

Genetic results are reported as a diplotype, which includes one maternal and one paternal allele (e.g., CYP2D6*1/*4). In some cases, patients have more than two copies of the CYP2D6 gene; up to 13 gene copies have been described. Those alleles are denoted by an "xN" following the allele designation, e.g., CYP2D6*2x2 (duplication). Additional details about allele nomenclature and definitions can be found at https://www.pharmvar.org, and information regarding the effects of allelic variation on CYP2D6 substrates can be found at the Pharmacogenomics Knowledgebase (https://www.pharmgkb.org/vip/PA166170264). CYP2D6 allele frequencies differ substantially among racial and ethnic groups.

The combination of alleles is used to determine a patient's diplotype. CYP2D6 alleles are characterized as wild-type (normal function), reduced-function, or nonfunctional alleles based on the expected activity of the enzyme that they encode. Each allele is assigned an activity value, i.e., 0 for nonfunctional, 0.5 for reduced-function, or 1.0 for fully functional forms (Gaedigk, 2008, *Clin Pharmacol Ther,* 83:234-42). Examples of allelic variants and CYP2D6 enzyme activity are shown in Table 2.

TABLE 2

| Functional Status | Activity Score | Alleles[a] |
|---|---|---|
| Functional/normal activity/wild-type | 1 | *1, *2, *27, *33, *35, *45, *46, *39, *48, *53 |
| Reduced-function/ decreased activity | 0.5 | *9, *10, *17, *29, *41, *49, *50, *54, *55, *59, *69, *72 |

TABLE 2-continued

| Functional Status | Activity Score | Alleles[a] |
|---|---|---|
| Non-functional, variant, or mutant/no activity | 0 | *3, *4, *5, *6, *7, *8, *11, *12, *13, *14, *15, *16, *18, *19, *20, *21, *31, *36, *38, *40, *42, *44, *47, *51, *56, *57, *62 |

[a]*1 is defined as wild-type. See https://www.pharmvar.org for nomenclature updates.

If multiple copies of the CYP2D6 gene are detected, the activity score is multiplied by the number of copies of each allele present. The total CYP2D6 activity score is the sum of the values assigned to each allele, which typically ranges from 0 to 3.0 but may exceed 3.0 in rare cases.

The phenotype is assigned based on the CYP2D6 activity score for the diplotype. Two phenotype assignment schemes are in use: Crews and Genelex. Examples of phenotypes assigned to the diplotype according to each scheme are shown in Table 3.

TABLE 3

| CYP2D6 Allele 1 | CYP2D6 Allele 2 | CYP2D6 Diplotype | CYP2D6 Activity Score | Scheme 1 (Crews) | Scheme 2 (Genelex) |
|---|---|---|---|---|---|
| *1 | *1xN | *1/*1xN | ≥3.0 | UM | UM |
| *2x2 | *41 | *2x2/*41 | 2.5 | UM | UM |
| *1 | *2 | *1/*2 | 2.0 | EM (normal) | EM (normal) |
| *1 | *17 | *1/*17 | 1.5 | EM (normal) | EM (normal) |
| *2 | *3 | *2/*3 | 1.0 | EM (normal) | IM |
| *1 | *4x2 | *1/*4x2 | 1.0 | EM (normal) | IM |
| *10 | *10 | *10/*10 | 1.0 | EM (normal) | IM |
| *4 | *10 | *4/*10 | 0.5 | IM | IM |
| *5 | *6 | *5/*6 | 0 | PM | PM |

EM: extensive (or normal) metabolizer; IM: intermediate metabolizer; PM: poor metabolizer; UM: ultra-rapid metabolizer.

The Crews phenotype assignment scheme is reported in Crews 2014. In the Crews phenotype assignment scheme, patients with an activity score of 0 are poor metabolizers (PMs, individuals carrying no functional alleles), those with a score of 0.5 are considered intermediate metabolizers (IMs, individuals carrying one reduced-function and one nonfunctional allele), those with a score of 1.0, 1.5, or 2.0 represent a range of extensive (or normal) metabolizers (EMs, individuals carrying two alleles encoding full or reduced function; or one full-function allele together with either one nonfunctional or one reduced-function allele), and those patients with a score >2.0 are classified as ultra-rapid metabolizers (UMs, individual carrying more than two copies of functional alleles). Drugs that require CYP2D6 for activity such as codeine and tramadol, will lack efficacy in PMs and possibly have a poor response in IMs (Crews 2014).

The Genelex phenotype assignment scheme (genelex.com) is the same as the Crews assignment scheme, except that those with a score of 1.0 are classified as IMs.

Predicted metabolizer phenotypes of common diplotypes under the Crews scheme are shown in Table 4.

TABLE 4

| CYP2D6 Allele | *1 | *2 | *1xN or *2xN | *3 | *4 or *4xN | *5 | *6 | *10 | *17 | *41 |
|---|---|---|---|---|---|---|---|---|---|---|
| *1 | EM | EM | UM | EM | EM | EM | EM | EM | EM | EM |
| *2 |  | EM | UM | EM | EM | EM | EM | EM | EM | EM |
| *1xN or *2xN |  |  | UM | EM or UM | EM or UM | EM or UM | EM or UM | UM | UM | UM |
| *3 |  |  |  | PM | PM | PM | PM | IM | IM | IM |
| *4 |  |  |  |  | PM | PM | PM | IM | IM | IM |
| *5 |  |  |  |  |  | PM | PM | IM | IM | IM |
| *6 |  |  |  |  |  |  | PM | IM | IM | IM |
| *10 |  |  |  |  |  |  |  | EM[a] | EM[a] | EM[a] |
| *17 |  |  |  |  |  |  |  |  | EM[a] | EM[a] |
| *41 |  |  |  |  |  |  |  |  |  | EM[a] |

[a] Some laboratories may define patients with these diplotypes as intermediate metabolizers.

The incidence of poor and ultra-rapid metabolizers varies greatly among populations (0-10% and 0-29%, respectively). Using the Crews classification scheme: Caucasians are 1-2% UMs, 5-10% PMs, 2-11% IMs, and 77-92% EMs (normals). Using the Genelex classification scheme, about 35% of Caucasians are IMs.

CYP2D6 is responsible for the metabolism of 25% of commonly used pharmaceuticals. In addition to CYP2D6 genetics causing inadequate CYP2D6 activity, CYP2D6 deficiency can also arise in patients who are co-prescribed inhibitor(s) of CYP2D6 (i.e., a patient co-prescribed a CYP2D6 inhibitor will become CYP2D6 deficient even if they have normal CYP2D6 genetics). Examples of CYP2D6 inhibitors include, but are not limited to, amiodarone (CORDARONE®), buprenorphine (SUBUTEX®), bupropion (WELLBUTRIN®), cannabidiol, celecoxib (CELEBREX®), chlorphenamine, chlorpromazine (THORAZINE®), chloroquine (ARALEN®), cimetidine (TAGEMET®), cinacalcet (SENSIPAR®), citalopram (CELEXA®), clemastine, clomipramine (ANAFRANIL®), diphenhydramine (BENADRYL®), doxepin, doxorubicin (ADRIAMYCIN®), duloxetine (CYMBALTA®), escitalopram (LEXAPRO®), fluoxetine (PROZAC®), halofantrine (HALFAN®), haloperidol (HALDOL®), hydroxyzine (ATARAX®), hyperforin (St. John's Wort), imatinib (GLEEVAC®), indinavir, levomepromazine, methadone (DOLOPHINE®), methylphenidate (RITALIN®), metoclopramide, mibefradil (POSICOR®), midodrine, moclobemide, mirabegron (MYRBETRIQ®), niacin (vitamin B3), niacinamide, paroxetine (PAXIL®), perphenazine (TRILAFON®), pimozide, promethazine, propafenone (RYTHMOL®), propoxyphene (DARVON®), quinidine (QUINIDEX®), quinine, ranitidine (ZANTAC®), ritonavir (NORVIR®), sertraline (ZOLOFT®), terbinafine (LAMISIL®), thioridazine (MELLARIL®), ticlopidine (TICLID®), tripelennamine (PYRIBENZAMINE®), and zuclopenthixol.

Examples of CYP2B6 inhibitors include orphenadrine (anticholinergic), clopidogrel (antiplatelet), clotrimazole (antifungal), curcumin (supplement and constituent of turmeric), ethinylestradiol (estrogen, contraceptive), fluoxetine (antidepressant), fluvoxamine (antidepressant), itraconazole (antifungal), ketoconazole (antifungal), memantine (NMDA antagonist), paroxetine (antidepressant), raloxifene (selective estrogen receptor modulator), sertraline (antidepressant), thioTEPA (anticancer) and ticlopidine (antiplatelet).

B. Desmetramadol

Tramadol and desmetramadol each exist as the trans conformational isomer, with each conformational isomer existing as a pair of enantiomers because two chiral centers are present in the cyclohexane ring of each compound. Accordingly, tramadol and desmetramadol each consist of an enantiomeric pair, designated (1R,2R)-tramadol, (1S,2S)-tramadol, (1R,2R)-desmetramadol, and (1S,2S)-desmetramadol. The (1R,2R) isomer is the positive (+) enantiomer, and the (1S,2S) isomer is the negative (−) enantiomer of each. Thus, the 1R,2R-isomer of tramadol, O-desmethyltramadol, desmetramadol and M1 is '(+)-tramadol', '(+)-O-desmethyltramadol', '(+)-desmetramadol' and '(+)-M1', respectively. The 1S,2S-isomer of tramadol, O-desmethyltramadol, desmetramadol and M1 is '(−)-tramadol', '(−)-O-desmethyltramadol', '(−)-desmetramadol' and '(−)-M1', respectively.

The terms "tramadol" and "desmetramadol" used herein without indication of the enantiomer shall mean the racemate.

Tramadol is commercially available from a variety of sources or may be made by the process described in U.S. Pat. No. 3,652,589 (incorporated by reference herein). Desmetramadol may be synthesized from tramadol by demethylation of tramadol according to methods in the art, using for example, DIBAL or Ph$_2$PH and an alkyl lithium compound (U.S. Pat. No. 6,780,891, incorporated by reference herein). Racemic desmetramadol may thus be obtained by demethylation of racemic tramadol, which is commercially available as a racemic mixture of the (R,R)- and (S,S)-enantiomers. Racemic tramadol may be resolved to yield its individual enantiomers and demethylated to yield the corresponding enantiomers of desmetramadol (U.S. Pat. No. 5,728,885, incorporated by reference herein). Thus, demethylation of (1R,2R)-tramadol will yield (1R,2R)-desmetramadol, and demethylation of (1S,2S)-tramadol will yield (1S,2S)-desmetramadol.

The enantiomers of tramadol HCl may be resolved using a modification of the procedure described in U.S. Pat. No. 3,652,589 (incorporated by reference herein), using D- or L-dibenzoyl tartaric acid (DBTA). Other methods that may be used for the resolution of enantiomers include formation of diastereoisomeric salts or complexes or derivatives which may be separated, for example, by crystallization, gas-liquid or liquid chromatography; selective reaction of one enantiomer with an enantiomer-specific reagent, for example, enzymatic oxidation or reduction, followed by separation of the modified and unmodified enantiomers; and gas-liquid or liquid chromatography in a chiral environment, for example, on a chiral support, such as silica with a bound chiral ligand or in the presence of a chiral solvent. It will be appreciated that where the desired enantiomer is converted into another chemical entity by one of the separation procedures described above, a further step is typically required to liberate the desired enantiomeric form. Alternatively, a specific enantiomer may be synthesized by asymmetric synthesis using optically active reagents, substrates, catalysts or solvents, or by converting one enantiomer to the other by asymmetric transformation.

As used herein, the terms "human", "subject", "human subject", or "patient" are used interchangeably and are intended to have equivalent meanings.

The term "pharmaceutically acceptable salts" means salts prepared from pharmaceutically acceptable non-toxic acids including inorganic acids and organic acids. Examples of acids that form pharmaceutically acceptable salts with desmetramadol include acetic acid, benzenesulfonic (besylate) acid, benzoic acid, camphorsulfonic acid, citric acid, ethenesulfonic acid, fumaric acid, gluconic acid, glutamic acid, hydrobromic acid, hydrochloric acid, isethionic acid, lactic acid, maleic acid, malic acid, mandelic acid, methanesulfonic acid, mucic acid, nitric acid, pamoic acid, pantothenic acid, phosphoric acid, succinic acid, sulfuric acid, tartaric acid and p-toluenesulfonic acid. The hydrochloric acid salt is particularly preferred.

The desmetramadol administered may be (1R,2R)-desmetramadol, (1S,2S)-desmetramadol, or a combination thereof, including the racemate. Preferably, the desmetramadol is the racemate, but the isolated isomers are also suitable according to the disclosure. In some embodiments, the amount of desmetramadol administered to a human is 5 mg to 200 mg, 5 mg to 100 mg, 5 mg to 50 mg, 5 to 25 mg, preferably 20 mg to 50 mg, and more preferably 10 mg to 40 mg. In other embodiments, the amount of desmetramadol administered is 5, 10, 15, 20, 25, 30, 35, 40, 45, 50, 55, 60, 65, 70, 75, 80, 85, 90, 95, 100, 110, 120, 140 and 160 mg. Preferred amounts of desmetramadol administered to a human are 5, 10, 15, 20, 25, 30, 35, 40, 45 and 50 mg. In preferred embodiments, the amount of desmetramadol or a pharmaceutically acceptable salt thereof administered to a human is 10 mg to 120 mg, 10 mg to 60 mg, 10 mg to 50 mg, 10 mg to 40 mg, and more preferably 10 mg to 30 mg. In embodiments involving administration every 4-6 hours, 10 mg to 30 mg is preferred. In embodiments involving administration every 12-24 hours, 30 mg to 120 mg is preferred. As will be known to one skilled in the art, these amounts can be scaled for administration to other mammals based on their body weight relative to the average adult human. Administration is preferably via the oral route.

As used herein, the term "disorder" modulated by opiate receptor activity and/or monoamine activity refers to a disorder, disease or condition where modulating opiate receptor activity and/or monoamine activity is an effective means of alleviating the disorder or one or more of the biological manifestations of the disease or disorder; or interferes with one or more points in the biological cascade leading to the disorder or responsible for the underlying disorder; or alleviates one or more symptoms of the disorder. Thus, disorders subject to modulation include the following.

(a) Disorders in which the lack of opiate receptor activity and/or monoamine activity is a cause of the disorder or one or more of the biological manifestations, whether the activity was altered genetically, by infection, by irritation, by internal stimulus or by some other cause;
(b) Disorders in which the disease or disorder or the observable manifestation or manifestations of the disease or disorder are alleviated by opiate receptor activity and/or monoamine activity. The lack of opiate receptor activity and/or monoamine activity need not be causally related to the disease or disorder or the observable manifestations thereof; or
(c) Disorders in which opiate receptor activity and/or monoamine activity interferes with part of the biochemical or cellular cascade that results in or relates to the disease or disorder. In this case, the opiate receptor activity and/or monoamine activity alters the cascade, and thus controls the disease, condition or disorder.

Disorders modulated by opiate receptor activity and/or monoamine activity include acute and chronic pain, neuropathic pain, affective disorders, including depression and anxiety, behavioral disorders, including attention deficit disorders, eating disorders, cerebral function disorders, substance abuse, urinary incontinence and premature ejaculation as those terms are defined in U.S. Pat. Nos. 6,780,891, 6,660,774 and 6,974,839, incorporated by reference herein. Most preferably, the disorder is acute pain, chronic pain or neuropathic pain. The term "neuropathic pain" is applied to any acute or chronic pain syndrome in which the sustaining mechanism for the pain is believed to involve abnormal transmission (peripheral) or processing (central) of somatosensory input.

The term "therapeutically effective amount" means, with respect to relieving pain, an amount (a) sufficient for the management of moderate to moderately severe pain in adults, (b) sufficient for the management of pain in adults that is severe enough to require an opioid analgesic and for which alternative treatments are inadequate, or (c) that causes subject-reported pain relief to improve by at least 0.4 points, at least 0.5 points, at least 0.6 points, at least 0.7 points, at least 0.8 points, at least 0.9 points, and most preferably by at least 1.0 points, on a 10 cm VAS or 10-point scale, where 0 indicates no pain and 10 indicates the worst pain imaginable to the patient. In other embodiments, "therapeutically effective amount" means, with respect to relieving pain, an amount that causes a subject to report an improvement in the quality of their daily life or an improvement in carrying out the functions of daily life.

The term "analgesia equivalent to tramadol" means that desmetramadol provides subject-reported pain relief that is substantially the same as the subject-reported pain relief provided by tramadol in normal and intermediate metabolizers. "Substantially the same" with respect to this definition means that (a) like tramadol, desmetramadol is also effective for the management of moderate to moderately severe pain in adults (scores of 5 or greater), (b) like tramadol, desmetramadol is also effective for the management of pain in adults that is severe enough to require an opioid analgesic and for which alternative treatments are inadequate, or (c) the average or individual subject-reported pain scores for desmetramadol and tramadol are not statistically different or differ from one another by less than 40%, 35%, 30%, more preferably by less than 25%, and most preferably by less than 15%.

"Safe" with respect to a therapeutically effective amount of desmetramadol means an incidence and severity of adverse events that is about the same as that arising from tramadol use in normal and intermediate metabolizers per its approved label and who are not otherwise administered CYP inhibitors.

The present disclosure relates to a method for relieving a disorder modulated by opiate receptor activity and/or monoamine activity. The method comprises orally administering to a human in need thereof the pharmaceutical composition containing a therapeutically effective amount of desmetramadol, or a pharmaceutically acceptable salt thereof. The method preferably comprises orally administering the pharmaceutical composition to a human in need thereof a therapeutically effective amount of desmetramadol or pharmaceutically acceptable salts thereof, without concurrently administering tramadol.

In one embodiment is a method for treating pain in a human, consisting of administering to a human subject in need thereof a dosage form consisting of a therapeutically effective amount of desmetramadol, or a pharmaceutically acceptable salt thereof as the sole active pharmaceutical ingredient. A preferred embodiment is a method for treating pain in a human subject, consisting of administering to a subject in need thereof a pharmaceutical composition consisting of a therapeutically effective amount of desmetramadol, or a pharmaceutically acceptable salt thereof, as the sole active ingredient, wherein the therapeutically effective amount of desmetramadol is 10 to 120 mg. In preferred embodiments the step of administering is repeated every 4 to 6 hours with 10 mg to 30 mg desmetramadol. In other preferred embodiments the step of administering is repeated every 12 to 24 hours with 30 mg to 120 mg desmetramadol. In a preferred embodiment detailed below, the pharmaceutical composition is a sustained release oral dosage form having a difference factor (f1) of 0 to 15 or a similarity factor (f2) of 50 to 100 for desmetramadol release in an in vitro dissolution, wherein the f1 and f2 reference values are 34% desmetramadol released at 1 hour, 50% desmetramadol released at 2 hour, 62% desmetramadol released at 3 hour, 71% desmetramadol released at 4 hour, 85% desmetramadol released at 6 hour and 93% desmetramadol released at 8 hour.

In some embodiments the method of administering desmetramadol further comprises one or more of the steps of measuring pain before and after administering desmetramadol, and measuring the change in pain. In preferred embodiments pain is measured using a 10 cm visual analog scale (VAS). In other embodiments pain is measured by a subject rating their pain (verbally, in writing or by pointing) on a verbal, written or visual point scale, e.g., a scale from 1 to 5, 1 to 10, or 1 to 100 points. Preferred descriptors for pain scales is 'no pain' for the lowest scale value, and the 'worst imaginable pain' for the maximum scale value. In other embodiments, pain is measured by asking the patient to report how the pain interferes with their daily life. In other embodiments the method comprises the additional step of measuring pain relief or change, wherein the magnitude of subject-reported pain relief (change) after desmetramadol administration is at least 0.5 points, at least 0.6 points, at least 0.7 points, at least 0.8 points, at least 0.9 points, and most preferably is at least 1.0 points, on a 10 cm VAS or 10-point scale. In other embodiments, pain relief is indicated by a subject reporting that the quality of their daily life has improved, or their ability to carry out the functions of daily life has improved.

In some embodiments the method comprises the step administering an inhibitor of CYP2D6 and/or CYP2B6 together with the desmetramadol. In this step, the term "together with" means the inhibitor of CYP2D6 and/or CYP2B6 is taken either before, concurrently with, or after the desmetramadol such that the inhibitor inhibits CYP2D6 and/or CYP2B6 while desmetramadol is providing pain relief.

In another embodiments, the method comprises the additional optional step of measuring the patient's CYP2D6 diplotype (i.e., genotype) either before or after administering the desmetramadol. In still other embodiments, the step of measuring a patients CYP2D6 genotype further comprises the steps of assigning a CYP2D6 activity score and/or phenotype. The phenotype may use any standard descriptor known in the art, including the descriptors of Scheme 1 or Scheme 2 (see above).

The desmetramadol administered is, for example, (1R, 2R)-desmetramadol, (1S,2S)-desmetramadol, a combination thereof, or most preferably the racemate. Such methods are particularly preferred in subjects in need of pain relief who are CYP2D6 poor metabolizers, CYP2D6 ultra-rapid metabolizers and who require administration of a CYP2D6 inhibitor together with desmetramadol, e.g., to treat the patient's depression and pain. Other preferred populations include subjects in need of pain relief who are younger the 12 years of age or who are younger than 18 years of age who have undergone surgery, including tonsillectomy and/or adenoidectomy.

C. Pharmaceutical Compositions

The present disclosure provides a pharmaceutical composition comprising a sustained release dosage form containing a pharmaceutically effective amount of an desmetramadol, or a pharmaceutically acceptable salt thereof, wherein the in vitro dissolution profile of desmetramadol from the pharmaceutical composition has a difference factor (f1) of 0 to 15, or a similarity factor (f2) of 50 to 100, when compared to the reference dissolution profile provided herein. Thus, the 'sustained release dosage form' refers to any material or combination of materials, or forms thereof, that result in an in vitro dissolution (i.e., release) profile for desmetramadol from a pharmaceutical composition that is the "same" as the reference dissolution profile (i.e., there is "sameness" with the reference dissolution profile, see section 'D. The Reference Dissolution Profile and Sameness' below). A tablet or capsule is preferred.

In preferred embodiments, the pharmaceutical composition will contain an additional active ingredient, for example, selected from the group consisting of acetaminophen (N-acetyl-p-aminophenol, paracetamol), aspirin, ibuprofen, diclofenac, naproxen, indomethacin, fenoprofen, oxycodone, hydromorphone, codeine, hydrocodone and topiramate, as provided in US20060147527, US20090130183, US20100010029, US20100104638, US20100196474 and U.S. Pat. Nos. 5,336,691, 5,516,803, 5,968,551 and 7,906,141, incorporated by reference herein, wherein the pharmaceutical composition is free of tramadol. A preferred additional active ingredient is a therapeutically effective amount of acetaminophen or ibuprofen. Preferred embodiments are tablets wherein acetaminophen is present in amounts from about 300 mg to 700 mg acetaminophen per unit, preferably from about 325 mg to about 650 mg per unit, e.g., tablets having 300, 325, 350, 400 or 500 mg per unit. Other preferred embodiment are tablets where ibuprofen is present in amounts from about 150 mg to 600 mg ibuprofen per unit, preferably from about 150 mg to about 300 mg per unit, e.g., tablets having 150, 200, 250 or 300 mg per unit.

In embodiments involving an additional active ingredient (e.g., acetaminophen), desmetramadol is preferably provided in a sustained release dosage form and the additional active ingredient is provided as an immediate release dosage form (e.g., each within discrete granules encompassed within the same capsule, wherein the desmetramadol granules provide sustained release, or alternatively as a multi-layer tablet, wherein one layer provides sustained release and the other layer provides immediate release). In other preferred embodiments of an oral dosage form, desmetramadol and additional active ingredient are both provided in a sustained release dosage form, wherein each form provides sustained release with the same or different kinetics (e.g., each within sustained release granules encompassed within the same capsule, or alternatively, both within the same monolithic sustained release tablet). The terms 'sustained release', abbreviated 'SR' and 'immediate release', abbreviated 'IR' are well known in the art.

The sustained release dosage form may take various forms, e.g., a monolithic tablet, particles of different sizes, pellets (or beads), phases within a larger unit such as layers or sections of other shapes within a larger unit (e.g., as in a multi-layer or a bull-eye tablet). A number of such formats and compositions, as well as the unit dosage forms in which these can be incorporated will be outlined in more detail hereinafter (see section 'D. Sustained Release Dosage Forms' below).

As used herein the term 'phase' refers to a defined three dimensionally shaped section in a tablet dosage form that contains the same material and wherein each phase is separated from the other. Examples of phases are layers, which are incorporated in bi- or multi-layer tablets. Other examples are cylindrical, spherical or other tri-dimensionally shaped sections that can be present in tablets. This gives rise to different tablet formats such as the so-called 'bull-eye' tablets, or concentric tablets (a central cylindrically shaped section completely surrounded with one or more further cylindrical layers (i.e. a ring-like combination), or 'coated' tablets wherein the coating is a layer completely surrounding a tablet nucleus and the like. Preference is given to bi- or multi-layer tablets in embodiments involving additional active ingredients, such as acetaminophen or ibuprofen.

In particular embodiments, the major part of desmetramadol or its salt form, and the additional active ingredient are in different phases of the pharmaceutical composition. In such embodiments, at least one phase may contain either the major part of the additional active ingredient or the major part of desmetramadol or a salt-form thereof. In particular embodiments, one phase contains the major part of desmetramadol or a salt thereof and another phase contains the major part of the additional active ingredient.

As used herein, 'major part' means that the major quantity of the desmetramadol or its salt form or of the additional active ingredient is present in a particular phase. Preferably the term 'major part' refers to a situation where at least more than about 90% of the concerned active ingredient is present in a particular phase, for example more than 95%, or more than 98%, or more than 99%, or even more than 99.5%. The same applies to particular forms, such as layers.

Most preferably, a phase containing one of both active ingredients should contain only a minute amount of the other active ingredient, or even none of the other active ingredient, for example a phase may contain the additional active ingredient and a minute amount, e.g., less than 1%, or less than 0.5% of desmetramadol or a salt form thereof, or vice versa.

Preferably a phase comprising desmetramadol or a salt form thereof is adjacent to a phase containing the additional active ingredient.

Tablets that are biphasic are preferred, but can also be multiphasic, e.g., having 3, 4, 5 or more phases. At least one layer should comprise desmetramadol or a salt form thereof, but in case of multiphasic tablets, more than one layer comprising desmetramadol or a salt form can be present. Phases that are layers are preferred.

The pharmaceutical composition is suitable for dosing every 2, 4, 6, 8, 10 or 12 hours, with every 4-6 preferred. More generally, the pharmaceutical composition can simply be dosed as needed for symptoms. The appropriate dosing frequency will give an effective blood plasma concentration of O-desmethyltramadol such that it is therapeutically effective to treat acute, chronic and neuropathic pain, and more generally, is effective for relieving a disorder modulated by opiate receptor activity and/or monoamine activity. The magnitude of a therapeutically effective dose typically varies with the nature and severity of the condition to be treated and the route of administration. The dose, and perhaps the dose frequency, will also vary according to the age, body weight and response of the individual patient. In general, the total daily dose of desmetramadol ranges from about 40 mg per day to about 200 mg per day, preferably about 60 mg per day to about 160 mg per day, and more preferably, about 80 mg per day to about 120 mg per day, in single or divided doses. It is further recommended that children, patients over 65 years old, and those with impaired renal or hepatic function, initially receive low doses and that the dosage is titrated based on individual responses and blood levels. It may be necessary to use dosages outside these ranges in some cases, as will be apparent to those in the art. Further, it is noted that the clinician or treating physician knows how and when to interrupt, adjust or terminate therapy in conjunction with individual patient's response.

D. The Reference Dissolution Profile and Sameness

The 'reference dissolution profile' for a pharmaceutical composition according to the disclosure herein is 34% desmetramadol released at 1 hour, 50% desmetramadol released at 2 hour, 62% desmetramadol released at 3 hour, 71% desmetramadol released at 4 hour, 85% desmetramadol released at 6 hour, and 93% desmetramadol released at 8 hour. The desmetramadol in the reference dissolution profile is preferably racemic desmetramadol or (+)-desmetramadol.

An approach accepted in the art to ensure the in vitro and in vivo sameness of a dissolution profile to a reference dissolution profile uses a difference factor (f1) or a similarity factor (f2) to compare the two profiles (FDA Guidance for Industry. *SUPAC—IR: Modified Release Solid Oral Dosage Forms—Scale-up and Post-Approval Changes: Chemistry, Manufacturing and Controls, In Vitro Dissolution Testing, and In Vivo Bioequivalence Documentation,* 1997; FDA Guidance for Industry. *Extended Release Oral Dosage Forms: Development, Evaluation, and Application of In Vitro/In Vivo Correlations,* 1997; FDA Guidance for Industry. *Dissolution Testing of Immediate Release Solid Oral Dosage Forms,* 1997). The difference factor (f1) calculates the percent (%) difference between the two curves at each time point and is a measurement of the relative error between the two curves:

$$f_1 = \{[\Sigma_{t=1}^{n} |R_t - T_t|] / [\Sigma_{t=1}^{n} R_t]\} \cdot 100$$

where n is the number of time points, $R_t$ is the dissolution value of the reference at time t, and $T_t$ is the dissolution value at time t of the dissolution profile being compared to the reference. The similarity factor (f2) is a logarithmic reciprocal square root transformation of the sum of squared error and is a measurement of the similarity in the percent (%) dissolution between the two curves:

$$f_2 = 50 \cdot \log\{[1 + (1/n)\Sigma_{t=1}^{n}(R_t - T_t)^2]^{-0.5} \cdot 100\}$$

Preferably, three or more dissolution time points are compared, and preferably no more than one time point in the comparison has greater than 85% desmetramadol released. An in vitro dissolution profile is considered the same as a reference dissolution profile when f1 is 0 to 15, and/or f2 is 50 to 100 (inclusive of limits). That is, there is considered to be in vitro and in vivo "sameness" between a pharmaceutical composition and the reference when f1≤15, and/or f2≥50. Sameness of a pharmaceutical composition means it will be bioequivalent to a pharmaceutical composition having the reference dissolution profile. More preferably, f1 should be close to 0 and f2 should be close to 100. Sameness according to f1 or f2 does not rely on any single dissolution time point but utilizes a plurality of time points to characterize the entire shape of a dissolution curve and whether it is the 'same' as the reference dissolution profile.

Thus, a pharmaceutical composition as specified herein will comprise a sustained release dosage form containing a pharmaceutically effective amount of desmetramadol, and optional additional active ingredients, or pharmaceutically acceptable salts thereof, wherein the in vitro dissolution profile of desmetramadol from the pharmaceutical composition has a difference factor (f1) of 0 to 15, or a similarity factor (f2) of 50 to 100, when compared to a reference dissolution profile of 34% desmetramadol released at 1 hour, 50% desmetramadol released at 2 hour, 62% desmetramadol released at 3 hour, 71% desmetramadol released at 4 hour, 85% desmetramadol released at 6 hour, and 93% desmetramadol released at 8 hour.

In vitro dissolution is preferably measured using the USP Apparatus I Basket Method at 75 rpm in buffer, preferably at 37° C. The volume of buffer is preferably 900 mL. The buffer pH is preferably 1.2, 4.5, 6.8 or 7.2. Suitable buffers include 0.1N HCl; pH 1.2, 0.05M acetate buffer; pH 4.5 and 0.05M potassium phosphate buffer; pH 6.8 or 7.2. Other dissolution media can include simulated gastric fluid or simulated intestinal fluid, each with or without enzymes.

E. Sustained Release Dosage Forms

Sustained released dosage forms (i.e. controlled release dosage forms) are well known in the art, and Chapter 94 of Remington: The Science and Practice of Pharmacy, entitled "Sustained-Release Drug Delivery Systems," describes the more common types of oral and parenteral sustained-release dosage forms. The relevant disclosure, Chapters 84 and 96, is incorporated herein by reference. It will be apparent to one skilled in the art how to prepare a pharmaceutical composition comprising a sustained release dosage form containing a pharmaceutically effective amount of an desmetramadol, or a pharmaceutically acceptable salt thereof, wherein the in vitro dissolution profile of desmetramadol from the pharmaceutical composition has a difference factor (f1) of 0 to 15, or a similarity factor (f2) of 50 to 100, when compared to the reference dissolution profile provided herein.

In general, sustained release may be achieved using any of three broad categories of delivery: (1) sustained release from a matrix, (2) sustained release from a reservoir and (3) sustained release from coated-beads and multi-particulates.

Sustained Release from a Matrix. Where the matrix is a sustained release it may comprise suitable digestible hydrophilic or hydrophobic polymeric or non-polymeric materials.

Examples of such polymeric materials are hydrophilic or hydrophobic polymers, such as polysaccharides, in particular gums (further in particular pH dependent gums), cellulose ethers (e.g., hydroxypropylmethyl cellulose, hydroxypropyl cellulose), especially alkylcelluloses, in particular $C_1$-$C_6$ alkyl cellulose, especially ethyl cellulose, acrylic resins, protein-derived materials, polyalkylene glycols, polyalkylene oxides, polysaccharide gums such as xanthan gum, and the like. Preferred are polymers such as polyvinyl acetate and polyvinylpyrrolidone and mixtures thereof, in particular the mixture known as KOLLIDON® SR which is polyvinyl acetate (8 parts w/w) and polyvinylpyrrolidone (2 parts w/w).

Examples of suitable polyakylene oxides are provided in US2011/0038930, and include polyalkylene oxide, polymethylene oxide, polyethylene oxide, polypropylene oxide, ethylene oxide-propylene oxide co-polymer, polyethylene, polypropylene, polyvinyl chloride, polycarbonate, polystyrene, polyvinylpyrrolidone, poly(alk)acrylate, poly(hydroxy fatty acids), such as for example poly(3-hydroxy-butyrate-co-3-hydroxyvalerate) (BIOPOL®), poly(hydroxyvaleric acid); polycaprolactone, polyvinyl alcohol, polyesteramide, polyethylene succinate, polylactone, polyglycolide, polyurethane, polyamide, polylactide, polyacetal (e.g., polysaccharides optionally with modified side chains), polylactide/glycolide, polylactone, polyglycolide, polyorthoester, polyanhydride, block polymers of polyethylene glycol and polybutylene terephthalate (POLYACTIVE®), polyanhydride (polifeprosan), copolymers thereof, block-copolymers thereof, and mixtures of at least two of the stated polymers. The polymers preferably have a molecular weight of at least 0.5 million, determined by rheological measurements. In a preferred embodiment, the molecular weight ranges from 1-15 million. Thermoplastic polyalkylene oxides, such as polyethylene oxides, with a molecular weight of at least 0.5 million, preferably up to 15 million, determined by rheological measurements, are particularly preferred. Preferably the polyalkylene oxide comprises a hot-melt extruded pharmaceutical composition that when formed provides sustained release of M1, and optionally a dosage form with a breaking strength of at least 500 N.

Examples of non-polymeric materials that can be used are digestible lipids having a long chain alkyl moiety, which may be straight or branched, saturated or unsaturated, substituted or unsubstituted. Of particular interest are $C_{8-50}$, especially $C_{12-40}$ lipids. Examples comprise fatty acids, fatty alcohols, glyceryl esters of fatty acids, mineral and vegetable oils and waxes. Lipids having a melting point of between 25 and 90° C. are preferred.

The sustained release form may conveniently contain between 1% and 95%, 10% and 95%, in particular from 10% to 90%, and in particular from 20% to 80% (by weight) of one or more hydrophilic or hydrophobic polymers or digestible lipids. In embodiments where the polymeric material is a mixture of polyvinyl acetate and polyvinylpyrrolidone and mixtures such as KOLLIDON® SR or a polysaccharide gum such as xanthan gum, alginate or gum Arabic, the preparation preferably contains between 20% and 90%, in particular from 30% to 80% (by weight). As used herein, 'alginate' refers to alginate or its salts, in particular to its alkali metal salts such as sodium or potassium salts. In embodiments containing polyalkylene glycols and polyalkylene oxides, the preparation preferably contains up to 60% (by weight) of a particular polymer. In further particular embodiments, the preparation may contain up to 60% (by weight) of at least one digestible, long chain lipid.

Of interest are sustained release matrixes comprising xanthan gum optionally in mixture with other gums, in particular with other pH dependent gums such as, for example, alginate.

Optionally, the sustained release matrix may also contain other pharmaceutically acceptable ingredients (excipients) which are conventional in the pharmaceutical arts such as diluents (e.g., lactose), lubricants (e.g., magnesium stearate), binders (e.g., microcrystalline cellulose), granulating aids, colorants, flavorants, surfactants, pH adjusters, anti-adherents and glidants (e.g., colloidal silica), and plasticizers (e.g., dibutyl sebacate) and other suitable ingredients (e.g., ammonium hydroxide, oleic acid). Preferred sustained release systems are described in U.S. Pat. No. 6,090,411 and US20130011444A1, incorporated herein by reference.

The sustained release form may conveniently be film coated using any film coating material conventional in the pharmaceutical art. A film coat is added, e.g., as a finish, for coloring purposes or taste masking or a combination of these. Preferably an aqueous film coating is used.

Alternatively, the sustained release form may comprise an immediate or sustained release matrix, as a core, and further having a controlled release coating. In such embodiments the immediate release core may be prepared via procedures known in the art, e.g., by a suitable granulation process followed by compression, or by direct compression, followed by a coating step with a coating material that ensures controlled release. In such preparations, the immediate release section or core of the preparation may contain any of the usual ingredients usually employed to make such immediate release sections or cores. Any of the ingredients mentioned herein with respect to excipients (i.e., carriers) used for immediate release forms can be employed. In the case of a sustained release core, such embodiments may be prepared via the methods herein, followed by a coating step with a coating material that ensures controlled release.

The sustained release profile of desmetramadol, and optionally also an additional active ingredient, can be adjusted in a number of ways. For instance, a higher loading of the drug will be associated with increased initial release rates. By selecting particular ingredients and by controlling the relative amounts thereof in the preparation it is possible to adjust the release profile of desmetramadol. Such particular ingredients, are for example, the matrix materials mentioned above, e.g., the polymeric materials mentioned above.

Matrix-based sustained released dosage forms suitable for providing sustained release of desmetramadol, and optional additional active ingredients (e.g., acetaminophen) released in either immediate release or sustained release, are provided in US20070183980A1, US20090280174A1, US20090130183A1, US20100010029A1, US20090175937A1, US20090238873A1, US20100104638A1, US20100196474A1, US20110038930A1, US20130011444A1, U.S. Pat. Nos. 5,427,799, 5,580,578, 5,591,452, 6,090,411, 6,143,327, 6,245,357, 6,254,887, 7,074,430, 7,611,730, 7,906,141 and 8,114,383, incorporated by reference herein.

Sustained Release from a Reservoir. In further embodiments, the sustained release form comprises a reservoir containing the active ingredient or active ingredients, or a plurality of reservoirs each containing one or more active ingredients. Reservoir devices usually consist of a semi-permeable barrier that is involved in the release of the active ingredient from a central site within the tablet. The manufacturing process may involve incorporating laser-bored orifices in the semi-permeable membrane. Representative sustained release forms comprising a reservoir are disclosed in for example U.S. Pat. No. 6,245,357. Other sustained release forms comprising a reservoir include for example an osmotic dosage form for delivering various drugs to a patient is presented in U.S. Pat. Nos. 3,845,770 and 3,916,899. The dosage forms disclosed in these patents are manufactured, for example, comprising a wall that surrounds a compartment comprising a drug with an exit in the wall for delivering the drug to a patient. In U.S. Pat. Nos. 4,008,719, 4,014,334, 4,058,122, 4,116,241 and 4,160,452 are made available dosage forms comprising an inside and an outside wall made of poly(cellulose acylate) for delivering a dosage of drug to a patient in need thereof.

Sustained Release from Bead and Multi-Particulates. In further embodiments, the sustained release form comprises spherical pellets containing the active ingredient and a spheronizing agent. The same active ingredient may also be blended in a plurality of sustained release forms so as to provide a blend of spherical pellets with differing dissolution rates for extended release or pulsatile release. The pellets may be film-coated or not. The spheronizing agent may be any suitable pharmaceutically acceptable material, which can be spheronized together with the active ingredient to form pellets. The term 'spherical pellet' is meant to comprise pellets, beads or spheroids that are more or less of regular shape. In particular embodiments the shape is round or about round, i.e. having or approaching the shape of a small sphere.

The average size of the pellets may vary but preferably the diameter is in the range of about 0.1 mm to 3 mm, in particular from about 0.5 mm to about 2 mm, more preferably about 1 mm.

The size distribution of the pellets may vary but in general it is preferred that it has limited variation. It may vary within a range of 10 to 20%. The size distribution may vary in a statistical manner, i.e. in a bell-shaped curve wherein e.g., 90% or, e.g., 95% of the number of pellets are within a size range that varies between about 10% to about 20% of the average sizes mentioned above.

The active ingredient (i.e., desmetramadol and an optional additional active ingredient) or its pharmaceutically acceptable salt is present in an amount, which is in the range of from about 0.1 to about 50%, in particular from about 1 to about 40%, more in particular from about 10 to about 35%, w/w relative to the total weight of the pellet.

The pellets may further comprise an appropriate carrier (i.e., excipient) which may be any carrier known in the art used for making pellets. Particular carrier materials are spheronizing agents that may be any suitable pharmaceutically acceptable material, which may be spheronized together with the active ingredient to form pellets. A preferred spheronizing agent is microcrystalline cellulose. The microcrystalline cellulose used may suitably be, for example, the product sold under the trade name 'AVI-CEL™'. The spheronizing agent is present in an amount, which is in the range of from about 25% to about 90%, in particular from about 35% to about 70% w/w, relative to the total weight of the pellet.

Optionally the pellets may contain other pharmaceutically acceptable ingredients such as binders, bulking agents and colorants. Suitable binders, some of which may also contribute to the sustained release properties of the pellets, include water-soluble polymers, e.g., water-soluble hydroxyalkyl celluloses such as hydroxypropyl cellulose and hydroxypropylmethyl cellulose, or water insoluble polymers, such as acrylic polymers or copolymers, or alkyl celluloses such as, for example, ethylcellulose. Suitable bulking agents include lactose or colloidal silicon dioxide. The amount of these other ingredients in the pellets will be relatively small, e.g., lower than 30%, or 20%, or even lower than 10% or 5% w/w relative to the total weight of the pellet.

The pellets for use in the preparations of some embodiments are made by an extrusion process followed by spheronization. The mixture used in the extrusion process comprises active ingredient, a suitable carrier material and other optional ingredients, and a suitable lubricant. The lubricant usually is water and the mixture for extrusion typically is converted into a granulate. After extrusion, the extrudate is spheronized to obtain pellets. If desired, the latter may be coated with a suitable coating material.

If the active ingredients act as an additional binder in the mixture that is extruded and spheronized (i.e., form a sticky mass upon contact with water and/or the other excipients used in the extrudate mixture), the addition of a dry lubricant will be preferable. Apart from providing lubrication, the dry lubricant also allows the material to be extruded at a much lower moisture content thereby reducing the sticking observed in the spheronizer.

Further embodiments thus are spherical pellets for sustained release comprising desmetramadol or a salt thereof, or desmetramadol and an additional active ingredient or salts thereof, a spheronizing agent and dry lubricant. In a further aspect, said pellets have a low water content. If desired, the pellets may be coated.

The dry lubricant in particular is a mono-, di- or triglyceride, or mixtures thereof. Suitable mono-, di- or triglycerides are the mono-, di- or triesters of glycerine and one or more fatty acids. The mono-, di- or triglycerides may contain the same or different fatty acid residues or mixtures thereof, e.g., technical mixtures obtained from saponification of natural oils. Of particular interest are fatty acid triglycerides wherein the fatty acid residue has from 12 to 30 carbon atoms and is saturated or partially unsaturated or may be substituted, e.g., with one or more hydroxy functions. Preferred are mono-, di- or triglycerides derived from $C_{18-30}$ fatty acids, in particular derived from $C_{22-26}$ fatty acids. Of particularly preferred interest are behenic acid mono-, di- or triglycerides.

The dry lubricant preferably is solid at room temperature and has a melting point or melting range which is in the range of 60° C. to 90° C., in particular is in the range of 70° C. to 80° C. A particularly suitable dry lubricant is the glyceride mixture sold under the trade name 'COMPRITOL™888ATO' which is a mixture of glyceryl mono-, di- and tribehenate, the dibehenate fraction being predominant, and having a melting range of about 69-74° C.

Preferably, the dry lubricant is selected such that it does not impact the dissolution behavior of the active ingredient.

The dry lubricant is present in an amount, which is in the range of from about 2% to about 50%, in particular between 10% and 35% w/w, relative to the total weight of the pellet.

Of particular interest are pellets that have low water content. In particular embodiments, the water contents in the pellets is lower than 5%, more in particular lower than 3%, w/w relative to the total weight of the pellet.

The spherical pellets, containing a dry lubricant, can be prepared by a process comprising extruding a mixture of the active ingredient with a suitable carrier in the presence of a dry lubricant and spheronizing the extrudate, wherein the dry lubricant is a triglyceride. The amount of dry lubricant in this mixture may vary but in general is comprised between 10% and 35% (w/w). A small amount of water may be added to the mixture. In a particular execution, the amount of water is 5% or lower, or 3% or lower, or 1.5% or lower, w/w, relative to the total weight of the mixture for extrusion. In a specific process the pellets are subsequently coated with a suitable coating.

The ingredients may be mixed together in any given sequence. In one embodiment, the dry lubricant is added to a mixture of active ingredient and the carrier material at room temperature. The mixture is subsequently extruded through a small orifice. The diameter of the latter is in relation to the size of the pellets that are eventually produced from the extrudate. In one embodiment, the diameter of the orifices is in the range of 0.5 mm to 2.0 mm. The extrusion may be done at slightly elevated temperature but preferably is performed without applied heating. The extruded material is subsequently placed into a spheronizer where it is spun at high speed.

In specific embodiments of the disclosure herein, the pellets (or spheroids), with or without dry lubricant, are subsequently coated with a suitable coating using art known methods. The coating can either be a functional coating or a diffusion controlling coating.

A functional coating may be applied for e.g., taste masking, protection of the pellets, to have improved stability (shelf-life) or for identification (for example by coloring). Functional coating often will be film coating, using any film coating material conventional in the pharmaceutical art. Preferably an aqueous film coating is used.

Diffusion controlling coatings are designed to achieve a target release profile such as controlled or sustained release permitting release of the active ingredient at a controlled rate in an aqueous medium. Suitable controlled or sustained release coating materials include water-insoluble waxes and polymers such as polymethacrylates, for example EUDRAGIT™ polymers, or water insoluble celluloses, in particular alkyl celluloses such as ethylcellulose. Optionally, water-soluble polymers such as polyvinylpyrrolidone or water-soluble celluloses such as hydroxypropylmethyl cellulose (HPMC) or hydroxypropyl cellulose (HPC) may be included. Further components that may be added are water-soluble agents such as polysorbate. Of particular interest is ethylcellulose (EC). Preferably, a suitable plasticizer is added. A coating material that is particularly suitable is the coating material sold under the trade name SURELEASE™ (Colorcon), which is a dispersion of ethylcellulose.

Alternatively, the active ingredient or its salt-form may be coated onto inert beads, in particular onto sugar beads, and the drug loaded beads coated with a material, which permits control of the release of the active ingredient into the aqueous medium.

Because of the bitter taste of one or more of the active ingredients, the pellets may be coated for taste-masking purposes although this may be of less importance if the pellets are used in a capsule dosage form.

Placement of Active Ingredients in the Dose Form. The additional active ingredient can be present throughout the pharmaceutical compositions disclosed herein, or in particular sections thereof. In particular embodiments, it is present in one or more phases. Preferably, the additional active ingredient is present in one or more phases that do not contain desmetramadol.

The phases can take a variety of forms, e.g., sections in a tablet, or they can take the form of pellets. These forms can be prepared following art-known procedures. In the particular case of sections in a tablet preparation, procedures can be applied such as granulation followed by partial or complete compression, or direct partial or complete compression.

Usually, the additional active ingredient is formulated into a suitable formulation. This is prepared by mixing the additional active ingredient with suitable ingredients to prepare different formulations such as powders, granulates, pellets and the like. The powder or granulate formulations may be compressed partially or completely to form appropriate phases for incorporation in bi- or multi-phasic preparations. Particular phases are layers for incorporation in bi- or multi-layer tablets. Most preferably, the additional active ingredient formulation will be for immediate release, i.e., the ingredients and the formulation form are selected such that release of the additional active ingredient (e.g., acetaminophen or ibuprofen) is as quickly and as complete as possible. Ideally, release is 100% after a short period of time, e.g., within ½ hour.

In tablet preparations, suitable tableting excipients may be added, e.g., one or more of the standard excipients such as diluents, lubricants, binding agents, flow aids, disintegrating agents, surface active agents or water soluble polymeric materials. Suitable diluents are, e.g., microcrystalline cellulose, lactose and dicalcium phosphate. Suitable lubricants are, e.g., magnesium stearate and sodium stearyl fumarate. Suitable binding agents are, e.g., hydroxypropyl methyl cellulose (hypromellose), polyvidone and methyl cellulose. Suitable disintegrating agents are starch, sodium starch glycolate, crospovidone and croscarmellose sodium. Suitable surface active agents are POLOXAMER® 188, Polysorbate 80 and sodium lauryl sulfate. Suitable flow aids are talc, colloidal anhydrous silica.

Double Layer Tablets. One particular execution of the pharmaceutical compositions of the present disclosure are double layer (or bilayer) tablets. These comprise one layer containing desmetramadol dispersed in a suitable sustained release dosage form, and another layer that contains the additional active ingredient (e.g., acetaminophen or ibuprofen).

The additional active ingredient containing layer preferably is composed of excipients typically used for oral dosage forms containing that active ingredient. Examples of such excipients comprise any of those mentioned above in relation to immediate-release formulations.

The desmetramadol layer comprises any of the sustained release dosage forms described above. The desmetramadol layer may contain from about 5 mg to 120 mg desmetramadol per unit, preferably from about 5 mg to about 75 mg, 5 mg to about 50 mg, 5 mg to about 40 mg, 5 mg to about 30 mg, 5 mg to about 25 mg, 5 mg to about 20 mg, 5 mg to about 15 mg, or from about 5 mg to about 10 mg per unit.

In particular embodiments, the desmetramadol layer contains a therapeutically effective amount of desmetramadol, or a pharmaceutically acceptable salt thereof, dispersed in a matrix, wherein the matrix contains from about 5% to about 95%, from about 10% to about 95% or from about 15% to about 95% of a polymer material selected from those above, wherein the percentage is w/w relative to the total weight of the sustained release dosage form.

The desmetramadol layer may additionally contain further ingredients such as the ingredients mentioned previously, including in particular starches, kaolin, lubricants, binders, carriers, lubricants, e.g., magnesium stearate, flow enhancers or fillers, e.g., silica (silicon dioxide), cellulose, fillers such as sugars, in particular lactose, titanium dioxide and the like. The concentration of magnesium stearate in the desmetramadol layer may vary, but good results are obtained in amounts ranging from about 0.5 to about 1.5% (w/w relative to the total weight of the sustained release dosage form). The concentration of microcrystalline cellulose in the desmetramadol layer may vary but good results are obtained in amounts which range from about 5% to about 80%, preferably from about 10% to about 65%, more preferably from about 20% to about 50% (w/w relative to the total weight of the sustained release dosage form).

The desmetramadol layer can be prepared by mixing desmetramadol or its salt form with polyvinyl acetate and polyvinylpyrrolidone, more in particular with the mixture thereof, still more in particular with KOLLIDON® SR while adding optional ingredients. The latter may also be added after the mixing of desmetramadol and KOLLIDON® SR. The thus obtained mixtures are subsequently compressed, either by direct compression, which is preferred or by preparing a granulate and subsequent compression.

Tablets of desmetramadol and polyvinyl acetate and polyvinylpyrrolidone mixtures can be prepared by direct compression. The mixtures for direct compression preferably contain a lubricant, in particular magnesium stearate. They may additionally contain a filler, in particular, a sugar such as lactose. They may furthermore contain a flow enhancer (i.e., a glidant) such as colloidal silica (silicon dioxide). In the mixtures for direct compression the lubricant preferably is present in concentrations in the range of about 0.5% to about 1.0%. The filler is present in concentrations from about 5% to about 80%, preferably from about 10% to about 65%, more preferably from about 20% to about 50%. The flow enhancer is present in concentrations from about 0.4% to about 1.5%, preferably about 0.5% to about 1.0%. All percentages herein are w/w relative to the total weight of the desmetramadol containing phase or phases.

Particular embodiments are coated tablets, in particular film-coated tablets. Coated tablets are easier to swallow than uncoated tablet cores, are usually easier to distinguish from other tablet, in particular when the film-coat contains a dye or a pigment and may furthermore have an improved stability (shelf-life). In the present instance, coating is mainly for taste masking because of the bitter taste of desmetramadol. Coatings are applied using art known methods using art known materials usually applied for this purpose. Particularly attractive coating products are based on suitable film-forming polymers such as hydroxypropylmethyl cellulose (HPMC) or polyvinyl alcohol (PVA). Preferably, a plasticizer is added. Examples of suitable plasticizers are polyethylene glycol or derivatives thereof such as polyethoxylated alkylglycerides, e.g., polyethoxylated stearyl monoglyceride, in particular the material sold under the trade name MACROGOL™. Further ingredients may be added to the coating such as fillers, dyes or pigments, flavors, sweeteners and the like components. Examples of such further ingredients are lactose, titanium dioxide, starch and the like. Particularly suited as coating materials are the OPADRY™ materials which mainly contain the before mentioned materials and further ingredients such as plasticizers, e.g., polyethylene glycol.

In a preferred embodiment, first the desmetramadol layer is produced by direct compression whereupon granules of the additional active ingredients (e.g., acetaminophen or ibuprofen) are placed on top of the compressed desmetramadol layer as to form a second layer whereupon the whole is compressed to form a bi-layer tablet.

In particular embodiments there are provided bi-layer tablets comprising an desmetramadol layer and an additional active ingredient layer, wherein both layers are separated by a suitable layer that may function as an isolator. This third layer may be comprised of suitable inert materials such as cellulose or lactose. Such embodiments may be prepared by first producing the desmetramadol layer by partial or complete compression of a suitable desmetramadol containing mixture, whereupon the isolator material is put on the desmetramadol layer followed by a second compression, where after a suitable additional active ingredient-containing mixture is put on top of the isolator layer as to form a third layer whereupon the whole is compressed to form a tri-layer tablet. The suitable desmetramadol containing mixture or suitable additional active ingredient-containing mixture may be a powder suitable for direct compression or a granulate obtained by a granulation process. The isolator layer may be desirable e.g., to avoid certain interactions between the components in each layer or to shield off humidity.

Multi-Layer Tablets. Further embodiments are multi-layer tablets having multiple layers of desmetramadol and an additional active ingredient, optionally separated by one or more isolator layers.

Further Tablet Formulations. In still further embodiments are desmetramadol tablets coated with a coating contain an additional active ingredient (e.g., acetaminophen or ibuprofen). In this preparation, a suitable core containing desmetramadol or a salt thereof in a sustained release dosage form is coated with an additional active ingredient-containing coating, e.g., by spraying with a suitable liquid formulation that contains the additional active ingredient. The core itself can be a tablet or another shaped phase.

Still further embodiments are so-called "bull-eye" tablets, which are tablets with a cavity in which another tablet fits. The tablet with the cavity may be U-shaped. The tablet with a cavity may contain the desmetramadol and the other tablet the additional active ingredient, or vice versa. Bull-eye tablets can be made following art-known procedures using specially adapted punches in a tableting machine.

In any of the preparations that are tablets, the latter may be coated with a suitable coating material.

Preparations with Pellets. Further embodiments are dosage forms comprising desmetramadol formulated in pellets, hereafter referred to as 'desmetramadol pellets.' The desmetramadol pellets may be prepared according to methods as described above and may be coated, if desired.

The desmetramadol pellets in turn may be coated with an additional active ingredient-containing coating, e.g., by spraying the desmetramadol pellets with an appropriate formulation containing the additional active ingredient. These desmetramadol pellets with an additional active ingredient-containing coating may be filled into capsules.

The desmetramadol pellets can be filled in capsules together with an appropriate formulation of the additional active ingredient, e.g., formulated as a powder, granulate, or formulated itself as a pellet. The desmetramadol pellets and the additional active ingredient formulation may be filled into the capsule in any give sequence, first the desmetramadol pellets followed by the additional active ingredient formulation or vice versa or the two together or the two together as a mixture.

In further embodiments there are provided capsules containing desmetramadol pellets and one or more additional active ingredient-containing tablets. The latter tablets will evidently be of such size and shape that it fits into a capsule. Preferably, only one tablet is filled into one capsule.

In still further embodiments there is provided a so-called 'capsule into capsule' dosage form, i.e., a capsule containing a suitable additional active ingredient-containing formulation is put into a bigger capsule containing desmetramadol pellets. Or vice versa, a capsule containing desmetramadol pellets is put into a bigger capsule containing a suitable additional active ingredient-containing formulation. A suitable additional active ingredient-containing formulation can be a powder or a pellet formulation.

Still other embodiments are sachets filled with amounts of desmetramadol pellets and a suitable additional active ingredient-containing formulation.

In still another aspect, an embodiment concerns a process for manufacturing a pharmaceutical dosage from, said method comprising filling the desmetramadol pellets into a suitable container and further adding a suitable additional active ingredient-containing formulation. In a preferred aspect the container is a capsule. Another type of container is a sachet.

A particular embodiment provides unitary dosage forms which comprise desmetramadol HCl pellets as described herein in an amount that is such that the dosage form contains an effective amount of desmetramadol HCl. Particular embodiments of such dosage forms may contain from about 10 mg to 100 mg M1 HCl per unit, preferably from about 10 mg to about 35 mg M1 HCl, from about 15 mg to about 75 mg, or from about 20 mg to about 50 mg of M1 HCl is per unit.

In general, all the compositions above may be presented in unit dosage form. Preferred unit dosage formulations are those containing a therapeutically effective dose, or an appropriate fraction thereof, of the active ingredient(s), or a pharmaceutically acceptable salt thereof.

Parenteral Dosage Forms. Parenteral immediate-release and sustained release dosage forms may also be used. Immediate and sustained (i.e. controlled) release parenteral formulations are well known in the art (e.g., incorporated herein by reference is the $19^{th}$ edition of *Remington: The Science and Practice of Pharmacy*, "Remington"). Chapter 94 of Remington entitled "Sustained-Release Drug Delivery Systems," describes the more common types of parenteral sustained release dosage forms (pages 1660-1675). Another sustained-release parenteral technology is Camurus' FluidCrystal® injection depot that comprises a lipid-based liquid with dissolved desmetramadol that can easily be injected subcutaneously using a conventional syringe with a thin needle. Upon contact with fluids in the tissue, the lipid solution transforms into a liquid crystalline gel, which effectively encapsulates the desmetramadol. Desmetramadol is slowly released as the liquid crystalline matrix gradually degrades in the tissue. The release can be controlled from several days to weeks or months depending on the composition. Other sustained-release parenteral technology is Alkermes' long-acting injectable technologies MEDISORB®, LINKERX® and NONCRYSTAL®. In preferred embodiments, the desmetramadol release profile in the body has a difference factor (f1) of 0 to 15 or a similarity factor (f2) of 50 to 100, wherein the f1 and f2 reference values are 34% desmetramadol released at 1 hour, 50% desmetramadol released at 2 hours, 62% desmetramadol released at 3 hours, 71% desmetramadol released at 4 hours, 85% desmetramadol released at 6 hours, and 93% desmetramadol released at 8 hours. The release profile preferably results in M1 pharmacokinetics that are substantially similar to the M1 pharmacokinetics arising from parenterally administered tramadol.

Other embodiments are directed to diluting the dose of desmetramadol in from about 50 mL to about 500 mL (and preferably from about 50 mL to about 100 mL) of a pharmaceutically acceptable fluid for injection such as normal saline, e.g., in a bag, and standardizing the administration of the injection of the dose of desmetramadol via the use of a pump. In another preferred embodiment, the dose of desmetramadol is provided in the form of a sterile solution at a concentration of about 10-30 mg desmetramadol hydrochloride/1 mL prior to dilution. In certain further preferred embodiments, the dose of desmetramadol prior to dilution is contained in one or more ampoules. In certain preferred embodiments, the ampoules contain the dose of desmetramadol (e.g., desmetramadol hydrochloride) together with a buffering agent (e.g., sodium acetate) in water for injection (e.g., about 1 mL to about 5 mL). In certain further preferred embodiments, the method further comprises diluting the dose of desmetramadol into an IV bag for administration to the patient.

A suitable pharmaceutically acceptable carrier for injection of desmetramadol in either an immediate-release (e.g., desmetramadol hydrochloride) or sustained-release dosage sterile form are well known to those of ordinary skill in the art. Examples include sterile water for injection, normal saline, and may include other ingredients beyond the dose of desmetramadol and the carrier/solvent for the desmetramadol, e.g., sterile solutions of simple chemicals such as sugars, amino acids or electrolytes, which can be easily carried by the circulatory system and assimilated. Such fluids are typically prepared with water for injection USP. Fluids used commonly for intravenous (IV) use are disclosed in Remington (citation above), and include: alcohol, e.g., 5% alcohol (e.g., in dextrose and water ("D/W") or D/W in normal saline solution ("NSS"), including in 5% dextrose and water ("D5/W"), or D5/W in NSS); synthetic amino acid such as AMINOSYN®, FREAMINE®, TRAVASOL®, e.g., 3.5 or 7; 8.5; 3.5, 5.5 or 8.5%, respectively; ammonium chloride e.g., 2.14%; dextran 40, in NSS e.g., 10% or in D5/W e.g., 10%; dextran 70, in NSS e.g., 6% or in D5/W, e.g., 6%; dextrose (glucose, D5/W) e.g., 2.5-50%; dextrose and sodium chloride e.g., 5-20% dextrose and 0.22-0.9% NaCl; lactated Ringer's (Hartmann's), e.g., NaCl 0.6%, KCl 0.03%, CaCl$_2$ 0.02%; lactate 0.3%; mannitol, e.g., 5%, optionally in combination with dextrose, e.g., 10% or NaCl, e.g., 15 or 20%; multiple electrolyte solutions with varying combinations of electrolytes, dextrose, fructose, invert sugar Ringer's, e.g., NaCl 0.86%, KCl 0.03%, CaCl$_2$ 0.033%; sodium bicarbonate, e.g., 5%; sodium chloride, e.g., 0.45, 0.9, 3, or 5%; sodium lactate, e.g., 1.6 M; and sterile water for injection. The pH of such IV fluids may vary, and will typically be from about 3.5 to about 8 as known in the art.

Parenteral desmetramadol contains 10 mg to 120 mg desmetramadol that may be administered as an immediate injection or as a slow bolus injection or infusion over a time period from 2-3 minutes, from 10 minutes to about 45 minutes, or from 1 hour to about 4 hours. Maintenance parenteral dosing may be on any frequency ranging from every 10-20 minutes to every 2-4 hours. Shorter maintenance intervals are preferably used as loading doses to attain a therapeutic level in the blood. In preferred embodiments, the therapeutic level of M1 in the blood is substantially the same as M1 in the blood after parenteral tramadol dosing but this is not required. One embodiment administers immediate-release desmetramadol as an initial injection of 20 mg infused over 2-3 min, followed by 20 mg every 10-20 minutes if necessary up to 120 mg for the first hour, with maintenance doses of 10 to 60 mg every 1 to 12 hours with a maximum dose of 180 mg daily. The administration can be by physician or patient controlled (e.g., PCA or 'patient controlled anesthesia').

The injectable desmetramadol dose is generally intended for in-hospital use, although it can be used in other settings. In certain preferred embodiments, the desmetramadol is administered intravenously over a time period from about 10 minutes to about 3 hours. In certain preferred embodiments, the therapeutically effective dose of desmetramadol is administered intravenously over a time period from about 10 minutes to about 45 minutes. Thus, in preferred embodiments, the therapeutically effective dose of desmetramadol is administered intravenously over a time period from about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 minutes. In preferred embodiments, the therapeutically effective dose of desmetramadol is administered intravenously over a time period from about 10 minutes to about 30 minutes. In other embodiments, desmetramadol is administered over a longer time period, e.g., from about 30 minutes to about 24 hours, and in certain embodiments preferably administered over a time period from about 24 to 48 hours in much slower infusion, e.g., from about 0.05 to about 2 ml per minute from a 100 ml-3 liter pre-mixed bag, providing a total desmetramadol dose over the course of the infusion from about 80 mg to about 320 mg, and preferably up to about 160 mg desmetramadol over about 24 hours, and from about 80 mg to about 640 mg desmetramadol over about 48 hours.

The invention is further illustrated by the following examples, which should not be construed as further limiting. The contents of all references, pending patent applications and published patents, cited throughout this application are hereby expressly incorporated by reference.

EXAMPLES

Example 1

Desmetramadol Analgesic Dosage Form

SR403 is a 10 mg desmetramadol tablet prepared through dry-blend and direct compression (Table 5). The physical characteristics: weight, thickness, hardness and friability were tested along with in vitro dissolution testing in various physiological relevant media of pH 1.2, 4.5 and 7.2. Dissolution was determined using a USP Type I dissolution assembly (VANKEL® VK-7000, Cary, N.C.) with a paddle speed of 75±0.1 rpm and bath temperature of 37.0±0.5° C. The dissolution buffers were 900 mL of 0.1N HCl; pH 1.2, 0.05M acetate buffer; pH 4.5 or 0.05M phosphate buffer; pH 7.2. Samples were detected on-line each hour throughout the duration of release using a UV/vis spectrophotometer at 270 nm (VARIAN CARY® 50, Cary, N.C.). Maximum absorbance values after a 1 hour infinity spin were used to calculate release. The dissolution kinetics were substantially independent of pH.

TABLE 5

| Components | | |
| --- | --- | --- |
| Desmetramadol HCl | Drug Substance | 10.0 mg |
| Microcrystalline cellulose | Binder/Flow Agent | 60.0 mg |
| HPMC K4M* | Wet Binder/Polymer | 60.0 mg |
| Sodium bicarbonate | Electrolyte | 30.0 mg |
| Magnesium stearate | Lubricant | 1.5 mg |
| | Tablet Weight | 161.5 mg |
| | Characterization | |
| | Appearance | White, round |
| | Friability | <0.1% |
| | Thickness (in) | 0.148 |
| | Hardness (kP) | 11.6 |
| | Dissolution in vitro | |
| | Hours to release 25% | 0.74 |
| | Hours to release 50% | 2.6 |
| | Hours to release 75% | 5.9 |
| | Hours to release 90% | 11.7 |

*HPMC, hydroxypropylmethyl cellulose.

Example 2

Clinical Trial Material

The SR403 10 mg tablet formulation was produced at a 6,000 and 55,000 tablet scale to yield clinical trial material (CTM) batches 3542-01 and 3823-12, respectively. In vitro dissolution was determined using a USP Type I dissolution assembly (DISTEK® Dissolution System, Evolution Model 6100) with a paddle speed of 75 rpm and bath temperature of 37.0±0.5° C. The dissolution buffer was 900 mL of 0.05M potassium phosphate buffer, pH 6.8. The amount of desmetramadol released over 12 hours dissolution was quantitated by HPLC. CTM batch 3542-01 has the in vitro reference dissolution profile (Table 6). There is in vitro and in vivo "sameness" between CTM batch 3823-12 and CTM batch 3542-01 because f1≤15, and f2≥50.

TABLE 6

| Time (hour) | % Desmetramadol Released (batch 3542-01) | % Desmetramadol Released (batch 3823-12) |
|---|---|---|
| 1 | 34 | 31 |
| 2 | 50 | |
| 3 | 62 | |
| 4 | 71 | 66 |
| 6 | 85 | |
| 8 | 93 | |
| 12 | 99 | 94 |
| f1 | — | 6.4 |
| f2 | — | 67 |

Example 3

Clinical Study

CTM batches 3542-01 and 3823-12 were used in a clinical study consisting of two trials A and B, respectively. The study tested whether desmetramadol alone could provide the same safety and analgesic profile to that provided by tramadol in humans who were normal metabolizers and intermediate metabolizers. The study also tested whether desmetramadol could provide this same profile even in humans made metabolically deficient by co-administration of the known powerful CYP2D6 and CY2B6 inhibitor paroxetine. It was unknown if desmetramadol could provide this profile in normal metabolizers, in intermediate metabolizers, in poor metabolizers, in ultra-rapid metabolizers, or in subjects co-administered an inhibitor of one or more CYP enzymes. Indeed, this is the first reported human clinical efficacy and safety study of desmetramadol.

Study Design

The study design consisted of two consecutive randomized, double-blind, three-period cross-over, placebo- and active comparator-controlled, single-center trials A and B performed between August 2014 and October 2014 and between October 2017 and December 2017 and conducted in a clinical research unit in Salt Lake City, Utah (ClinicalTrials.gov Identifiers: NCT02205554 and NCT03312777). The study was approved by an independent ethics committee and was conducted in accordance with the Declaration of Helsinki and other applicable guidelines, laws, and regulations. Written informed consent was obtained from all subjects.

Figure 2:
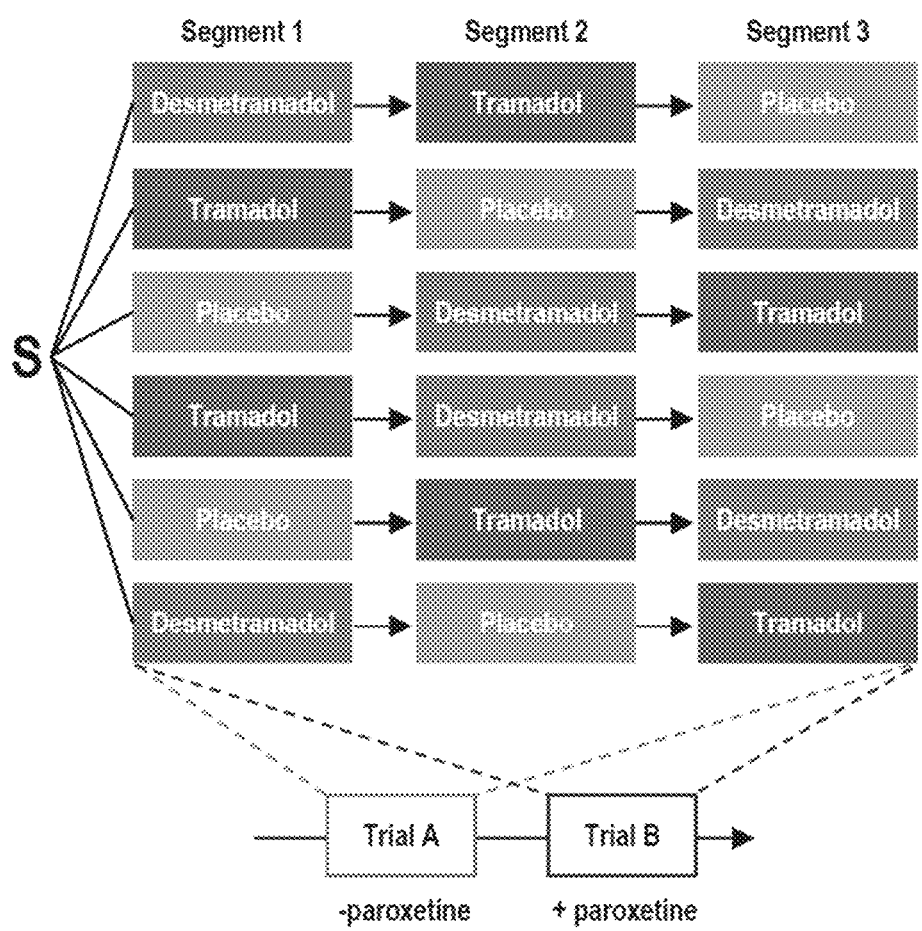
FIG. 2 shows the study design, wherein subjects (S) in trials A and B were randomized and administered six possible treatment sequences in which Segments 1, 2, and 3 are separated by one or two weeks, for trial A and B respectively. In each segment doses of each study drug were administered every six hours until nine doses were administered and steady-state levels are reached. After the ninth dose of each segment, cold-induced pain was assessed. All subjects in trial B additionally received daily paroxetine one day before each treatment segment.

After screening, subjects in both trials A and B were randomized to one of six possible treatment sequences of placebo, 50 mg tramadol (ULTRAM®; Janssen Ortho, LLC, Gurabo, Puerto Rico) and 20 mg desmetramadol (Syntrix Pharmaceuticals, Auburn, Wash.) (FIG. 2). Nine doses of each study drug were given every 6 hours in each of the three treatment segments, with segments separated by 1 week in trial A and 2 weeks in trial B. Subjects stayed at the clinical research unit during the entirety of each treatment segment and were discharged during the time between segments and at the end of the third segment. For one hour before, and one hour after doses eight and nine, the subject's diet (oral intake) was limited to clear liquids only. Subjects in trial B also received three consecutive 20 mg daily doses of paroxetine beginning one day before each treatment segment. Paroxetine levels were quantified by sampling blood immediately before the ninth dose of study drug in each treatment segment (QUEST DIAGNOSTICS™, West Valley City, Utah). End of study in both trials consisted of a telephone follow-up one week after the end of the third segment.

Randomization to the six treatment sequences was in a ratio of 1:1:1:1:1:1 using a computer-generated random list of permuted blocks of six. Blinding of study drug was by over-encapsulation.

Measurements were made to quantify steady-state plasma M1 and tramadol enantiomers by sampling blood immediately before and after the ninth dose of study drug. Cold-induced pain was measured in the cold pressor test after the ninth dose of study drug. Pupil diameter and abuse liability measures were assessed after the seventh dose of study drug in trial A. Adverse events and vital signs were collected throughout each trial.

Endpoints and Formal Study Hypothesis

Trial A: The primary endpoint consisted of the steady-state minimum ($Css_{min}$) and maximum ($Css_{max}$) plasma concentrations of (+)-tramadol, (−)-tramadol, (+)-M1 and (−)-M1. Secondary endpoints consisted of cold-induced pain, safety, abuse liability, pupil diameter and CYP2D6 genotype.

Trial B: The primary endpoint consisted of cold-induced pain perception or tolerance. Secondary endpoints consisted of $Css_{min}$ and $Css_{max}$, and safety.

The formal study hypothesis was that bioequivalent and equi-analgesic doses of tramadol and desmetramadol in trial A will produce significantly greater plasma (+)-M1 and superior analgesia for desmetramadol compared to tramadol in trial B where subjects are metabolically deficient.

Subjects

Eligible subjects were aged 18 and 50 years, of general good health, had a tolerance to cold-induced pain of ≥20 seconds and ≤120 seconds, and in trial B had a CYP2D6 genotype consistent with an intermediate metabolizer phenotype or normal metabolizer phenotype. Each subject's CYP2D6 genotype was determined using a multiplex PCR and allele-specific primer extension assay (xTAG™ Mutation Detection, LUMINEX® Molecular Diagnostics, Austin, Tex.) that identifies 17 variants (*1, *2, *3, *4, *5, *6, *7, *8, *9, *10, *11, *12, *14, *15, *17, *41, gene duplication) and two gene rearrangements (Genelex, Inc., Seattle, Wash.). The assay covers over 93-97% of poor metabolizer phenotypes and has an analytical specificity and sensitivity for detection of these mutations >99%. Trial A conserved power to detect tramadol and desmetramadol analgesia by enrolling only males because females exhibit large variation and temporal instability to repeated cold-induced pain.[40] Further criteria for key inclusion and exclusion criteria are presented in Table 7.

withdrawal and first pain were determined at 1, 2 and 3 hours after the ninth dose of each study drug and averaged.

Safety and Tolerability. Assessments of the safety and tolerability of desmetramadol and tramadol included: 1)

TABLE 7

Key Inclusion and Exclusion Criteria

| KEY INCLUSION CRITERIA | KEY EXCLUSION CRITERIA |
|---|---|
| Healthy male and female (trial B) adults up to 55 years old with normal blood pressure, pulse and respiration | History of seizures, epilepsy or recognized increase risk of seizure |
| Tolerance to cold-induced pain of ≥20 and ≤120 seconds | History of cirrhosis or laboratory evidence of liver disease |
| Negative urine for substances of abuse | Known or suspected alcohol or drug abuse within the past 6 months |
| Normal or intermediate CYP2D6 metabolizer (trial B) | Inhibitors of monoamine oxidase, serotonin and/or norepinephrine reuptake, and other medications or supplements known to induce or inhibit drug metabolism or that may affect the serotonergic nemotransmitter system |
| Adequate hematologic and liver function per pre-defined limits | |
| Cockcroft-Gault glomerular filtration rate ≥60 mL/min and urinalysis with ≤+1 glucose, +1 ketones, and +1 protein | |
| Body mass index (BMI) 18.0 to 32 kg/m | Ethanol, grapefruit, grapefruit-related citrus fruits (e.g., Seville oranges, pomelos), grapefruit-related juices or other new medication |
| If female of childbearing potential must use adequate contraception | |
| Electrocardiogram without clinically significant changes | Pregnant or breast feeding (trial B) |
| Negative serology for HIV, hepatitis B surface antigen and hepatitis C virus antibody | |

Assessments

Steady-State Pharmacokinetics. The $Css_{min}$ and $Css_{max}$ of (+)-tramadol, (−)-tramadol, (+)-M1 and (−)-M1 were measured by collecting blood immediately before the ninth study drug dose and at 1.0, 1.5, 2.0, 2.5 and 4.0 hours afterward. An additional sample was taken at 8.0 hours in trial B to measure the half-life. The tramadol and M1 enantiomers were quantified using a chiral liquid chromatography mass spectroscopy method using a LUX® Cellulose-2 (PHE-NOMENEX®, Calif.) chromatographic column and positive atmospheric pressure chemical ionization (APCI) mode while operating the instrument in the multiple-reaction-monitoring (MRM) mode. The assay was validated in accordance with FDA guidance. The lower limit of quantification for each enantiomer was 5.0 ng/mL. The calibration range was 5-1000 ng/mL for each enantiomer. Assay accuracy for (+)-M1 was 99.3-103% and the precision (relative standard deviation) was 0.8-3.6%. Assays were conducted in the bioanalytical laboratories of IITRI Life Sciences Group (Chicago, Ill.).

Pupillometry. Pupillary contraction measured by pupillometry is a pharmacodynamic marker of target engagement by opioids including tramadol. Pupil diameter was measured with a NEUROPTICS® VIP™ 200 Pupillometer (Laguna Hills, Calif.) before the first dose and after the seventh dose of each treatment segment.

Abuse Liability. Opioids induce positive responses in subjective measures of abuse in healthy subjects who are not abusing drugs. Abuse liability assessments were performed in trial A after the seventh dose that consisted of a 100 millimeter visual analog scale (VAS) for each of drug-liking-disliking, take-drug-again, and strength-of-drug-effect measures.

Analgesia. The cold pressor test is an established test model for evaluating analgesia. Pain intensity (0-10 cm VAS from no pain at 0 to worst pain imaginable at 10) at 30 seconds and at first perception, and time (seconds) to hand withdrawal and first pain were determined at 1, 2 and 3 hours after the ninth dose of each study drug and averaged.

adverse events (AEs) and serious AEs; 2) vital signs; 3) laboratory analyses; and 4) study drug discontinuation. AE's were allocated to a study drug if they occurred after its first dose and before either the first dose of the next study drug or the end of the study. The AE relationship to blinded study drug was assessed by the investigator as either not related, unlikely related, possibly related, probably related or definitely related. An AE was drug-related if it was designated as possibly, probably or definitely related. The severity of AEs were graded on an FDA-specified scale for healthy adult and adolescent volunteers. Vital signs included systolic and diastolic arterial blood pressures, pulse and respiratory rate. Vital signs were obtained at screening baseline and before and after each study drug administration in trial A. In trial B, baseline vital signs were obtained once for each segment before paroxetine administration, and then once after each paroxetine and study drug administration. Vital signs were obtained in trials A and B at the end of each treatment segment and before discharge.

Statistical and Computational Methods. The reported peak mean pain perception to cold before and after a single 50 mg dose of tramadol was used to power the first-in-man trial A (mean [SD] pain intensity before and after tramadol of 6.3 [2.0] and 5.0 [2.3] centimeters on a VAS, respectively) (Hagelberg, 2013, *Eur J Clin Pharmacol,* 69:867-75). To provide at least 80% power in trial A to detect a −1.3 centimeter change in pain perception between desmetramadol and placebo, a sample size of 39 subjects was planned. To provide at least 97% power in trial B to detect a −0.5 centimeter change in pain perception between desmetramadol and tramadol at 30 seconds, a sample size of 60 subjects was planned informed by trial A data. Formal statistical analysis plans were developed before unblinding trials A and B. All descriptive and inferential statistical analyses were performed using SAS® version 9.3 or R version 3.0. Continuous endpoints were analyzed using mixed-effects linear models. The appropriate covariance structure was selected using graphical tools and information criteria. In trial B, the overall analgesic analysis used a backwards selection approach to determine the significant effects with treatment, segment, sequence and gender as fixed effects and subject as a random effect nested within sequence. Segment was added as a fixed effect to find any significant first-order crossover effects. Otherwise, analyses used mixed effects linear models with treatment, segment and sequence as fixed effects and subject as a random effect nested within sequence. Segment was again added as a fixed effect to find any significant first-order crossover effects. If significant treatment effects were present, least-squares-means were compared between desmetramadol and placebo, or tramadol and placebo, using Dunnett's procedure, and between desmetramadol and tramadol using a paired t-test. In addition to overall analyses, separate analyses for measures of analgesia were performed for males and females. $Css_{min}$ was specified as the smallest and $Css_{max}$ as the largest value for each analyte in a segment. Bioequivalence was computed using the log-transformed $Css_{min}$ and $Css_{max}$ values for each enantiomer and claimed when the 90% confidence interval (CI) of their ratio was 0.8 to 1.25. The half-life ($t_{1/2}$) in trial B was computed using the elimination rate constant ($k_e$) and analyte concentrations $C_4$ and $C_8$ at hour 4 ($t_4$) and hour 8 ($t_8$), respectively, wherein $$k_e = (\ln C_4 - \ln C_8)/(t_8 - t_4) \text{ and } t_{1/2} = 0.693/k_e.$$

Missing data were confirmed to be missing completely at random and excluded without imputation. The hypothesized superior analgesia of desmetramadol to tramadol in trial B was tested using a 1-sided test at the 5% significance level. All other statistical comparisons were made using 2-sided tests at the 5% significance level and all CIs for bioequivalence were calculated with a 2-sided 90% confidence level.

The intention to treat (ITT) population included all subjects who were randomized to treatment and was stipulated to be the primary data set for analysis and statistical conclusions of significance. The per-protocol (PP) population was comprised of a subset of subjects from the ITT population who completed the study with no major protocol deviations. A major protocol deviation was one that could adversely affect the rights, safety or well-being of the subjects and/or the quality and integrity of data. Protocol deviations were assigned as being major or minor before unblinding. The efficacy population in trial B constituted subjects who received all drug doses and had cold pressor efficacy data from all three segments. A sensitivity analysis was performed by conducting the analyses for the ITT, PP and efficacy populations as defined. All results presented are for the ITT population; unless otherwise specified, results from the PP and efficacy population analyses supported those for the ITT population. The safety population included all patients who received study drug. All safety analyses were performed on the safety population.

Results

Figure 3:
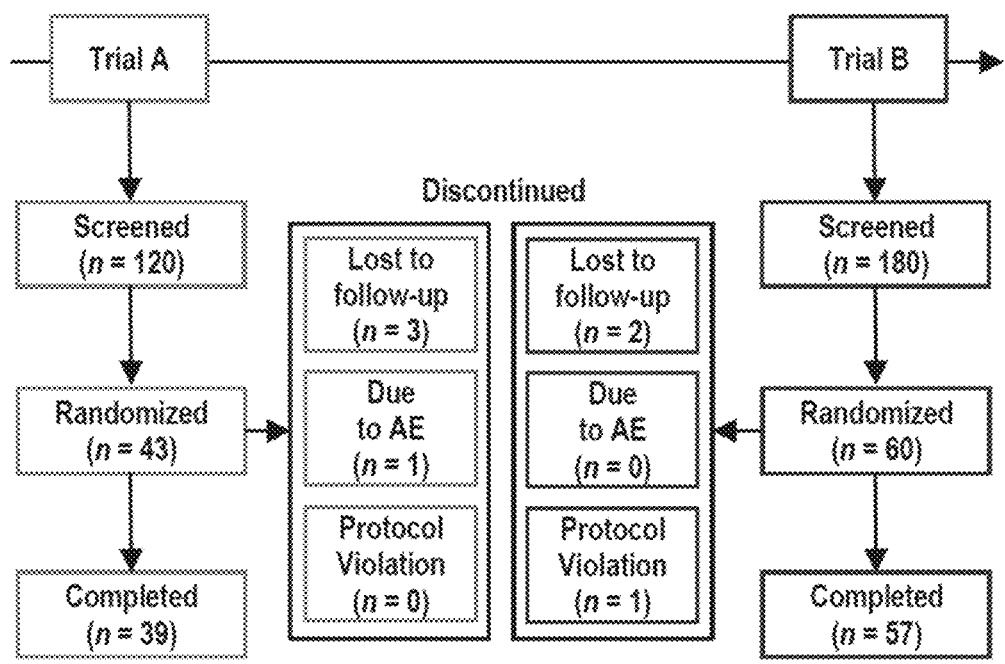
FIG. 3 shows subject flow and disposition in the clinical study. The number of subjects screened and randomized is shown for each trial, and the number of subjects completing the study is noted. Also shown is the number of subjects discontinuing the study and those discontinuing for adverse events (AE) or protocol violation.

Of the 300 subjects screened, 103 subjects were randomized in consecutive trials A and B at one clinical research unit in the United States (FIG. 3). All subjects who were randomized (the ITT population) received treatment with study drug and 96 (93%) completed the study. A total of 7 of the 103 subjects discontinued from the study after treatment was initiated. In the trial A cohort, 4 subjects discontinued; 1 discontinued due to AEs and 3 were lost to follow-up. In the trial B cohort, 1 subject was withdrawn because of a major protocol violation involving a urine test positive for a substance of abuse (cocaine) and 2 subjects were lost to follow-up. Subjects received 1,111 doses (96%) of 1,161 possible study drug doses in trial A, and received 1,575 doses (97%) of 1,620 possible study drug doses in trial B. Subjects with missing study drug doses were evenly distributed across placebo (A, B=2, 2), desmetramadol (A, B=1, 1) and tramadol (A, B=3, 2). All subjects in trial B received all planned paroxetine doses while on study, or 525 (97%) of 540 possible doses. Most subjects were Caucasian (92%) and baseline demographic characteristics such as age and body mass index were similar in both trial A and B cohorts (Table 8). Normal and intermediate CYP2D6 metabolizers constituted 96% and 100% of the trial A and B cohorts, respectively.

TABLE 8

Demographics and CYP2D6 Phenotype

| CHARACTERISTIC | TRIAL A (N = 43) | TRIAL B (N = 60) |
| --- | --- | --- |
| Age, years, M (SD) | 28.4 (8.0) | 28.0 (6.8) |
| Age range, years | | |
| Minimum | 21 | 18 |
| Maximum | 53 | 45 |
| Sex, n (%) | | |
| Male | 43 (100) | 42 (70) |
| Female | 0 (0) | 18 (30) |
| Race, n (%) | | |
| Caucasian | 39 (91) | 56 (93) |
| Asian | 3 (7) | 0 (0) |
| Black or African American | 0 (0) | 3 (5) |
| American Indian or Alaska Native | 1 (2) | 1 (2) |
| Ethnicity, n (%) | | |
| Hispanic or Latino | 6 (14) | 7 (12) |
| Not Hispanic or Latino | 37 (86) | 53 (88) |
| BMI, kg/m², M SD | 25.5 (3.1) | 24.8 (3.4) |
| BMI range, kg/m² | | |
| Minimum | 19.5 | 18.9 |
| Maximum | 31.8 | 31.7 |
| CYP2D6 activity score, n (%)* | | |
| 0.0 (Poor metabolizer) | 1 (2)** | 0 (0) |
| 0.5 (Intermediate metabolizer) | 0 (0) | 3 (5) |
| 1.0 (Intermediate metabolizer) | 17 (41) | 19 (32) |
| 1.5 (Normal metabolizer) | 7 (17) | 9 (15) |
| 2.0 (Normal metabolizer) | 16 (38) | 29 (48) |
| 3.0 (Ultra-rapid metabolizer) | 1 (2)** | 0 (0) |

Abbreviations: M, mean; SD, standard deviation.
*Phenotype using Scheme 2 (Genelex scheme).
**Subject 510 (poor metabolizer) and subject 523 (ultra-rapid metabolizer).

Figure 4A:
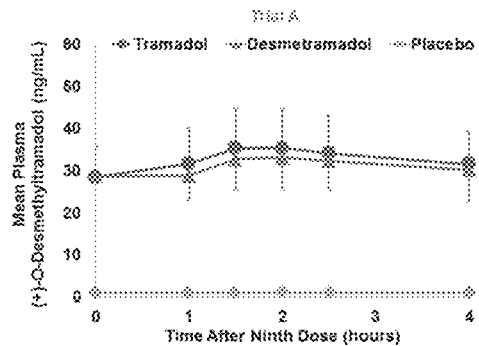
FIGS. 4A-4H shows mean steady-state plasma levels (ng/ml) of (+)-O-desmethyltramadol in trial A (FIG. 4A) and in trial B (FIG. 4E), (−)-O-desmethyltramadol in trial A (FIG. 4B) and in trial B (FIG. 4F), (+)-tramadol in trial A (FIG. 4C) and in trial B (FIG. 4G), and (−)-tramadol in trial A (FIG. 4D) and in trial B (FIG. 4H) for the period following the ninth dose (hours). In each panel, the results for trial A (n=43) and trial B (n=60) are shown for subjects administered tramadol (circles), desmetramadol (triangles), and placebo (diamonds). Bars show for standard deviation and with respect to plasma levels. Baseline points for plasma levels of subjects receiving the placebo are all below the quantitation limit.
Figure 4B:
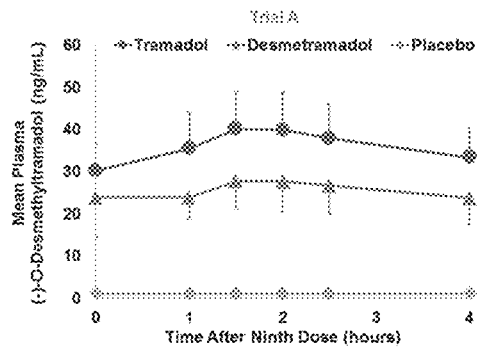
Figure 4C:
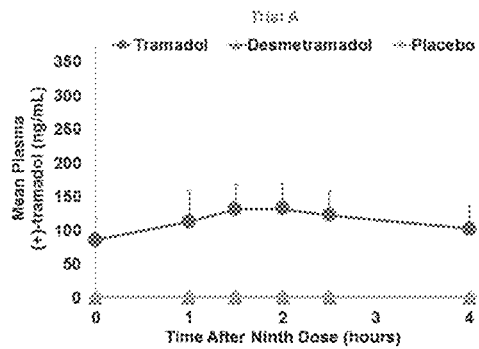
Figure 4D:
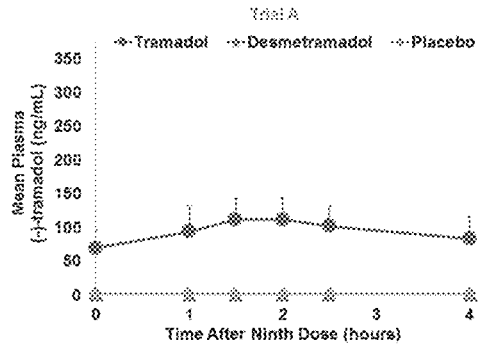

Steady-State Pharmacokinetics. In the absence of paroxetine (trial A), 20 mg desmetramadol dosed every six hours replicated the mean steady-state plasma profile of (+)-O-desmethyltramadol produced by 50 mg tramadol dosed at the same frequency (FIG. 4A). The desmetramadol and tramadol mean $Css_{min}$ and $Css_{max}$ for (+)-O-desmethyltramadol were statistically bioequivalent (mean [SD]=28 [7] vs 26 [6] and 37 [10] vs 36 [10] ng/mL; 90% CIs, 0.85-1.08 and 0.88-1.13, respectively; Table 9). $Css_{min}$ and $Css_{max}$ for (−)-O-desmethyltramadol were 30% lower for desmetramadol compared to tramadol and just outside statistical bioequivalence (mean [SD]=30 [6] vs 21 [5] and 42 [9] vs 30 [9] ng/mL; 90% CIs, 0.69-0.76 and 0.67-0.76, respectively; FIG. 4B and Table 9). Desmetramadol produced no circulating tramadol enantiomers as expected (FIGS. 4C and 4D).

TABLE 9

Steady-State Pharmacokinetics and Paroxetine Level

| ANALYTE | TRIAL A (N = 43) | | TRIAL B (N = 60) | |
| --- | --- | --- | --- | --- |
| | TRAMADOL | DESME-TRAMADOL | TRAMADOL | DESME-TRAMADOL |
| (+)-O-desmethyltramadol | | | | |
| $Css_{min}$, ng/mL, M (SD) | 28 (7) | 26 (6) | 11 (6) | 38 (9) |
| 90% CI* | | 0.85-1.08 | | 3.4-4.3 |
| P-value | | | | <0.001 |
| $Css_{max}$, ng/mL, M (SD) | 37 (10) | 36 (10) | 14 (8) | 51 (11) |
| 90% CI | | 0.88-1.13 | | 3.4-4.3 |
| P-value | | | | <0.001 |
| Half-life, h, M (SD) | | | 18 (39) | 8 (6) |
| P-value | | | | 0.065 |
| (−)-O-desmethyltramadol | | | | |
| $Css_{min}$, ng/mL, M (SD) | 30 (6) | 21 (5) | 25 (7) | 25 (8) |
| 90% CI | | 0.69-0.76 | | 0.95-1.09 |
| P-value | | | | 0.64 |
| $Css_{max}$, ng/mL, M (SD) | 42 (9) | 30 (9) | 35 (10) | 35 (10) |
| 90% CI | | 0.67-0.76 | | 0.93-1.07 |
| P-value | | | | 0.79 |
| Half-life, h, M (SD) | | | 12 (8) | 7 (5) |
| P-value | | | | <0.001 |
| (+)-tramadol | | | | |
| $Css_{min}$, ng/mL, M (SD) | 85 (33) | ND | 183 (49) | ND |
| $Css_{max}$, ng/mL, M (SD) | 143 (36) | ND | 295 (62) | ND |
| Half-life, h, M (SD) | | | 8.6 (2.5) | ND |
| (−)-tramadol | | | | |
| $Css_{min}$, ng/mL, M (SD) | 68 (27) | ND | 140 (41) | ND |
| $Css_{max}$, ng/mL, M (SD) | 122 (32) | ND | 242 (56) | ND |
| Half-life, h, M (SD) | | | 7.2 (2.3) | ND |
| Paroxetine, ng/mL, M (SD) | NA | NA | 11 (8) | 12 (9) |

Abbreviations: M, mean; SD, standard deviation; h, hour; NA, not applicable; ND, not detected. *Pharmacokinetic parameter is statistically bioequivalent if 90% CI is within the range 0.80 to 1.25.

Figure 4E:
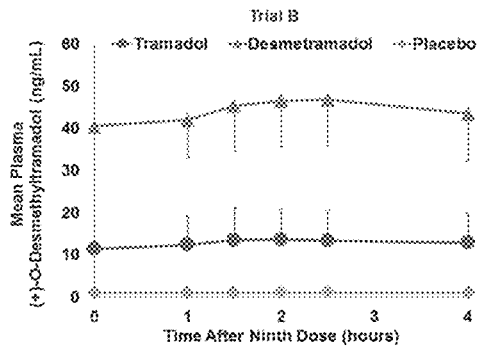

Paroxetine given in three daily 20 mg doses in trial B produced a similar level of circulating paroxetine in tramadol and desmetramadol dosed segments (mean [SD]=11 [8] vs 12 [9] ng/mL, respectively; Table 9). Compared to trial A, paroxetine in trial B depressed tramadol (+)-O-desmethyltramadol $Css_{min}$ (−61%) and $Css_{max}$ (−62%), but increased desmetramadol (+)-O-desmethyltramadol $Css_{min}$ (46%) and $Css_{max}$ (41%) (FIG. 4E vs 4A and Table 9). The paroxetine-induced changes in trial B caused desmetramadol $Css_{min}$ and $Css_{max}$ for (+)-O-desmethyltramadol to each significantly exceed by 3.5-fold the corresponding tramadol $Css_{min}$ and $Css_{max}$ (mean [SD]=38 [9] vs 11 [6] and 51 [11] vs 14 [8] ng/mL, respectively; P<0.001; Table 9). The (+)-O-desmethyltramadol half-life after tramadol dosing was double the half-life after desmetramadol dosing (mean [SD]=18 [39] vs 8 [6] hours; P=0.065).

Figure 4F:
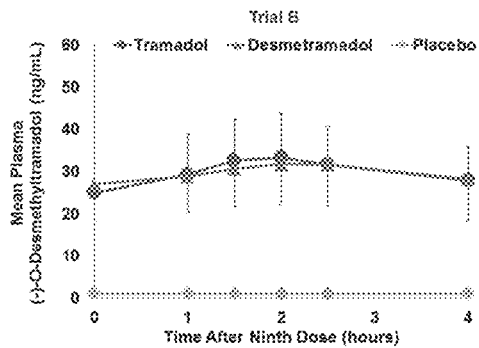

Paroxetine resulted in comparatively smaller changes for (−)-O-desmethyltramadol (FIG. 4F vs 4B). Compared to trial A, the (−)-O-desmethyltramadol $Css_{min}$ and $Css_{max}$ were decreased 17% for tramadol and increased 14-16% for desmetramadol in the presence of paroxetine (Table 9). The paroxetine-induced changes in trial B had the net effect of making desmetramadol and tramadol $Css_{min}$ and $Css_{max}$ for (−)-O-desmethyltramadol statistically bioequivalent (mean [SD]=25 [7] vs 25 [8] and 35 [10] vs 35 [10] ng/mL; 90% CIs, 0.95-1.09 and 0.93-1.07; Table 9). Like the positive enantiomer, the half-life of (−)-O-desmethyltramadol in trial B was greater for tramadol compared to desmetramadol (mean [SD]=12 [8] vs 7 [5] hours; P<0.001).

Figure 4G:
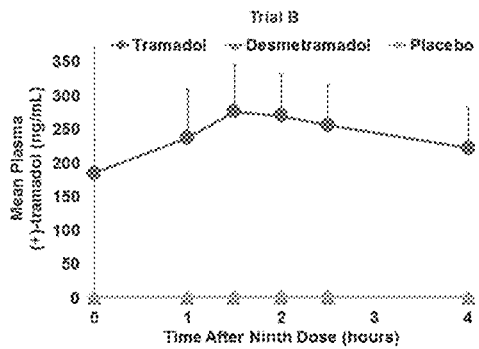
Figure 4H:
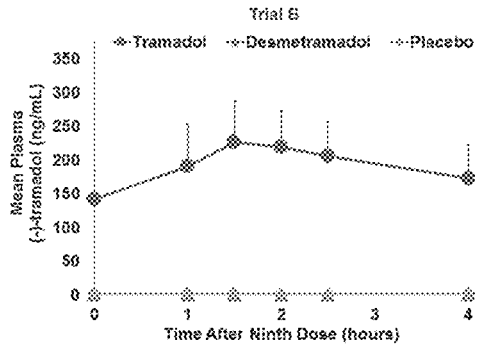
Figure 5A:
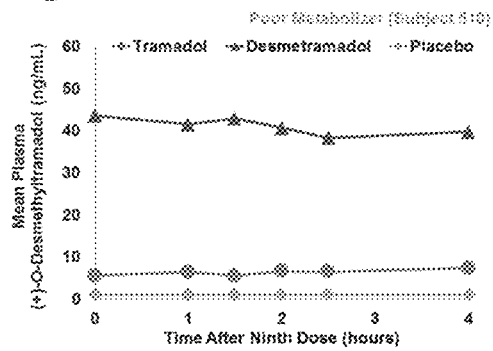
FIGS. 5A-5H shows the results of measuring mean steady-state plasma levels of (+)-O-desmethyltramadol in the poor metabolizer (Subject 510) (FIG. 5A) and in the ultra-rapid-metabolizer (Subject 523) (FIG. 5E), (−)-O-desmethyltramadol in the poor metabolizer (FIG. 5B) and in the ultra-rapid metabolizer (FIG. 5F), (+)-tramadol in the poor metabolizer (FIG. 5C) and in the ultra-rapid metabolizer (FIG. 5G), and (−)-tramadol in the poor metabolizer (FIG. 5D) and in the ultra-rapid metabolizer (FIG. 5H) in trial A. Plasma levels are shown for subjects administered tramadol (circles), desmetramadol (triangles), and placebo (diamonds). Baseline points for plasma levels of subjects receiving the placebo are all below the quantitation limit.
Figure 5B:
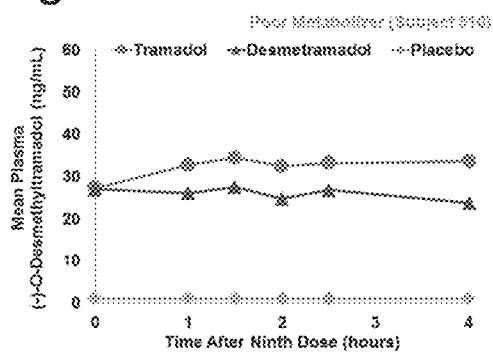
Figure 5C:
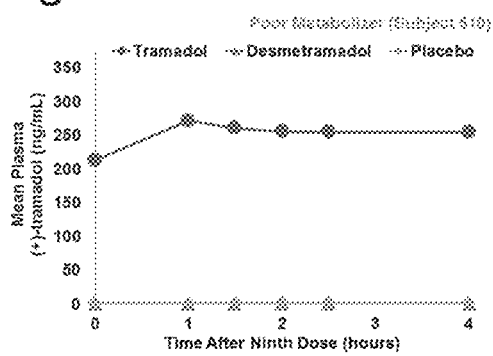
Figure 5D:
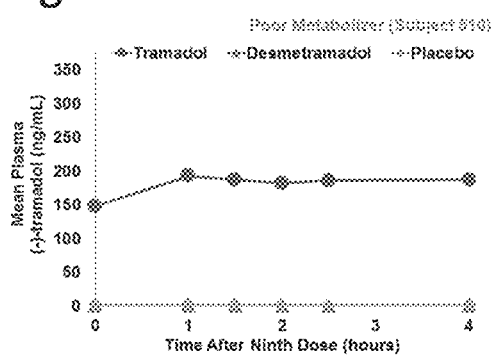
Figure 5E:
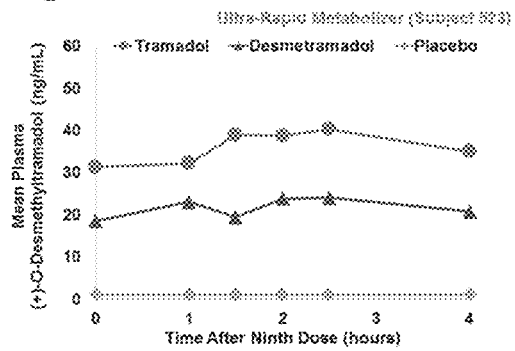
Figure 5F:
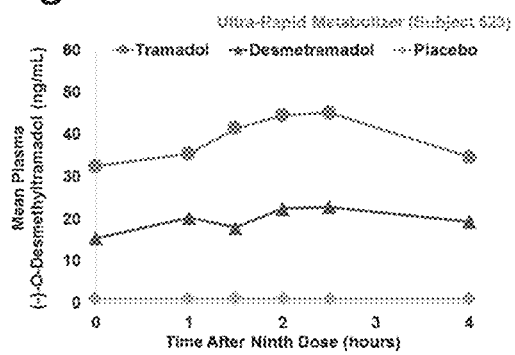
Figure 5G:
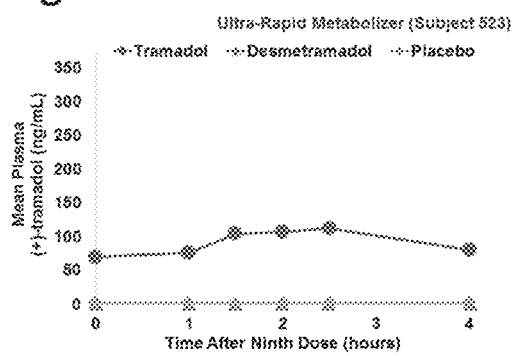
Figure 5H:
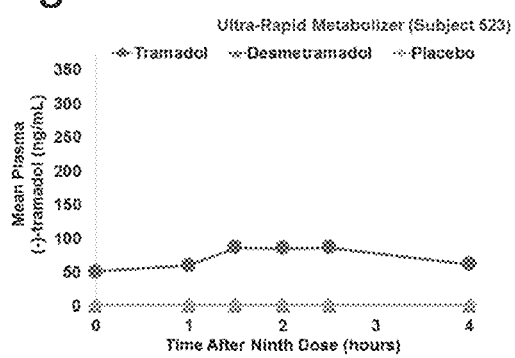

As in trial A, desmetramadol produced no circulating tramadol enantiomers in trial B (FIGS. 4G and 4H). However, compared to trial A, the mean steady-state (+)-tramadol and (−)-tramadol plasma concentration profiles after tramadol dosing were increased 2-fold in the presence of paroxetine, as were the $Css_{min}$ and $Css_{max}$ (FIGS. 4G vs 4C and 4H vs 4D; Table 9).

The $Css_{min}$, $Css_{max}$ and half-life had no statistically significant sequence or segment effects in either trial A or trial B. There was no carryover from segment to segment in either trial A or trial B as evidenced by no detectable O-desmethyltramadol or tramadol enantiomers in placebo treated segments, and no detectable tramadol enantiomers in desmetramadol treated segments.

Compared to mean tramadol (+)-O-desmethyltramadol in the poor metabolizer (subject 510) and ultra-rapid metabolizer (subject 523) of trial A, mean desmetramadol (+)-O-desmethyltramadol was increased 650% (41 vs 6.3 ng/mL) and decreased 40% (22 vs 36 ng/mL), respectively (FIGS. 5A-5H).

Pupillometry and Abuse Measures. The mean pre-dose pupil diameter in trial A was similar in placebo, tramadol and desmetramadol dosed segments (mean [SD]=6.1 [0.9], 6.1 [0.9] and 6.0 [1.1] millimeters, respectively; Table 10). After dosing, tramadol and desmetramadol each caused a significant reduction in pupil diameter compared to placebo (mean paired reduction [SD]=−0.7 (0.6) and −1.1 (0.8) millimeters; each P<0.0001).

Tramadol and desmetramadol dosing did not cause mean responses in the drug-liking-disliking and take-drug-again VAS to differentiate from placebo (Table 10). There was a significant treatment effect (P<0.0001) in the strength-of-drug-effect VAS and mean responses after tramadol and desmetramadol dosing were significantly elevated compared to placebo (mean [SD]=32 [29] vs 12 [8] and 29 [28] vs 12 [8] millimeters; P<0.001 and P=0.0004, respectively).

TABLE 10

Pupil Diameter and Abuse Measures

| | TRIAL A (N = 43) | | |
|---|---|---|---|
| | PLACEBO | TRAMADOL | DESME-TRAMADOL |
| Pupil Diameter, mm, M (SD) | | | |
| Pre-dose | 6.1 (0.9) | 6.1 (0.9) | 6.0 (1.1) |
| After seventh dose | 6.2 (1.0) | 5.5 (1.1) | 5.1 (1.2) |
| P-value vs placebo | | <0.0001 | <0.0001 |
| Abuse Measures, 0-100 mm, M (SD) | | | |
| Drug-liking-disliking | 49 (14) | 48 (15) | 47 (25) |
| P-value vs placebo | | NS | NS |
| Take-drug-again | 49 (19) | 47 (18) | 43 (26) |
| P-value vs placebo | | NS | NS |
| Strength-of-drug-effect | 12 (18) | 32 (29) | 29 (28) |
| P-value vs placebo | | <0.0001 | 0.0004 |

Abbreviations: mm, millimeter; M, mean; SD, standard deviation; NS, not significant.

Figure 6:
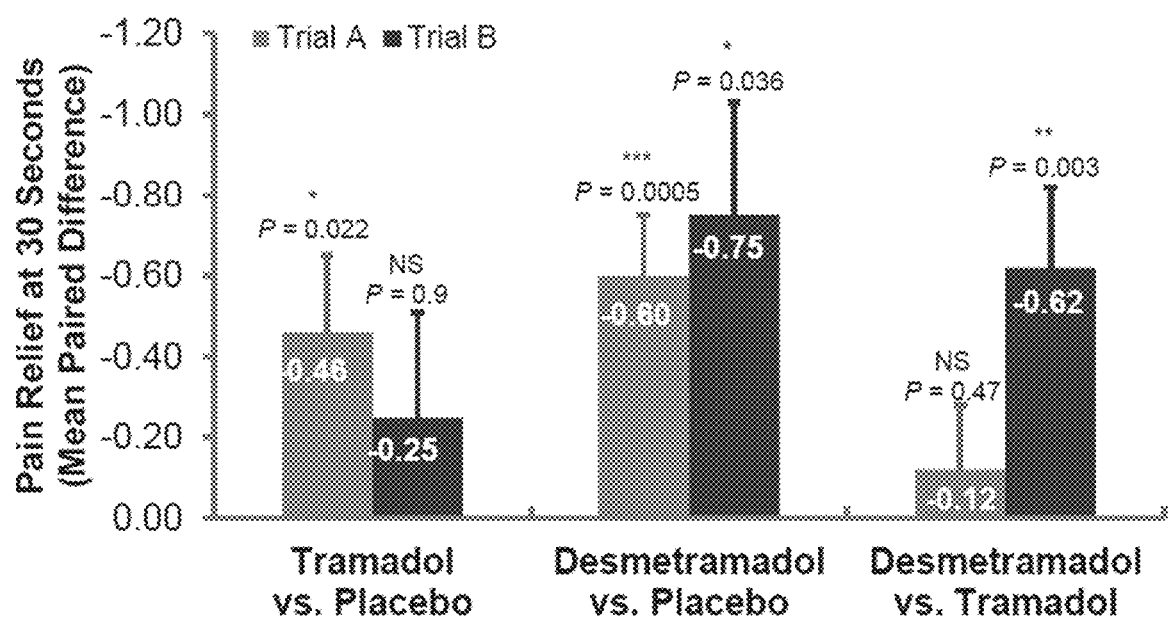
FIG. 6 shows the results of measuring cold-induced pain at 30 seconds for subjects in Trial A and Trial B. Pain relief in subjects who received tramadol or desmetramadol is compared to relief from those who received placebo, and to each other. Values for the wmean pain relief are given. Bars are standard error of the mean. P values are reported. Abbreviations: NS, not statistically significant; *, P<0.05; , P<0.01; *, P<0.001.

Analgesia. In the male population of trial A (n=43), there was a similar and statistically significant within-subject reduction in average cold-induced pain perception at 30 seconds in subjects treated with tramadol and desmetramadol compared with placebo (mean [SE]=−0.46 [0.19] and −0.60 [0.15]; P=0.022 and P=0.0005, respectively; FIG. 6). Average (SD) subject-reported pain scores at 30 seconds were 6.2 (1.8), 6.0 (1.7) and 5.8 (1.7) after placebo, tramadol and desmetramadol, respectively (i.e., desmetramadol and tramadol differed from one another by 0.2/6.0=3.3% or 0.2/5.8=3.4%, falling within "analgesia equivalent to tramadol" as defined above). Each treatment contained moderate (scores of 5 to 6) and severe (scores of 7 to 10) subject-reported pain scores. There was no significant difference between tramadol and desmetramadol in trial A (P=0.47). In the male population of trial B (n=42) treated identically as trial A except for the inclusion of paroxetine, tramadol failed to statistically differentiate from placebo (P=0.90). In contrast, desmetramadol provided pain relief that was statistically superior to both placebo (P=0.036) and tramadol (P=0.003). The average change in paired pain scores between desmetramadol and placebo, and between desmetramadol and tramadol were similar (mean [SE]=−0.75 [0.28] and −0.62 [0.20], respectively; FIG. 6). There was no significant treatment effect in the intensity of pain at first perception by subjects in either trial A or trial B (Table 11).

TABLE 11

Measures of Cold-Induced Pain

| PAIN MEASURE | TRAMADOL VERSUS PLACEBO | DESME-TRAMADOL VERSUS PLACEBO | DESME-TRAMADOL VERSUS TRAMADOL |
|---|---|---|---|
| Trial A (n = 43, males) Pain intensity, 0-10, MPD (SE) | | | |
| At 30 seconds | −0.46 (0.19) P = 0.015 | −0.60 (0.15) P = 0.0019 | −0.12 (0.16) P = 0.5 |
| At first perception | −0.21 (0.10) NS | −0.15 (0.09) NS | 0.07 (0.10) NS |
| Time, seconds, MD (SE) | | | |
| Withdrawal | 12.4 (4.4) P = 0.0076 | 12.6 (3.8) P = 0.006 | 0.03 (4.4) P = 1.0 |
| First pain | 2.1 (0.85) P = 0.029 | 2.6 (0.73) P = 0.0057 | 0.42 (0.93) P = 0.7 |
| Trial B (n = 42, males) Pain intensity, 0-10, MPD (SE) | | | |
| At 30 seconds | −0.25 (0.26) P = NS | −0.75 (0.28) P = 0.036 | −0.62 (0.20) P = 0.003 |
| At first perception | −0.08 (0.15) NS | −0.17 (0.14) NS | −0.09 (0.13) NS |
| Time, seconds, MPD (SE) | | | |
| Withdrawal | 6.9 (1.6) P = 0.001 | 9.9 (1.9) P < 0.001 | 2.8 (2.4) P = 0.126 |
| First pain | 1.5 (0.5) P = 0.013 | 2.1 (0.5) P = 0.001 | 0.6 (0.6) P = 0.193 |
| Trial B (n = 18, females) Pain intensity, 0-10, MPD (SE) | | | |
| At 30 seconds | 0.03 (0.78) NS | 0.28 (0.63) NS | 0.09 (0.35) NS |
| At first perception | 0.01 (0.21) NS | −0.24 (0.20) NS | −0.26 (0.26) NS |
| Time, seconds, MPD (SE) | | | |
| Withdrawal | 7.5 (4.2) NS | 8.2 (5.3) NS | 0.61 (8.0) NS |
| First pain | 2.6 (1.2) NS | 1.9 (0.8) NS | −0.7 (1.5) NS |

Abbreviations: MPD, mean paired difference; SE, standard error of the mean; NS, no significant treatment effect.

The average duration of tolerance to pain in trial A was similar for desmetramadol (63 seconds) and tramadol (62 seconds), and each was significantly greater than placebo (mean paired increase relative to placebo [SE]=12.6 (3.8) and 12.4 (4.4) seconds; P=0.006 and P=0.0076, respectively; Table 11). In the presence of paroxetine, male subjects in trial B tolerated pain 44% longer after desmetramadol than after tramadol (mean paired increase relative to placebo [SE]=9.9 (1.9) vs 6.9 (1.6) seconds; P<0.001 and P=0.001, respectively). In both trials the average time to the first perception of pain was similar for tramadol and desmetramadol, and each was significantly greater than placebo.

There was no significant treatment effect in the trial B female population (Table 11). The lack of statistically significant analgesia in the small trial B female population dosed with either tramadol or desmetramadol was expected a priori because normally menstruating women exhibit a variable and increasing cold-induced pain tolerance and threshold over repeated stimulation (Kowalczyk, 2006, J Pain, 7:151-60). Females were enrolled in trial B to collect data for the secondary safety and pharmacokinetic endpoints in both sexes. To ensure sufficient males would be enrolled to test the formal hypothesis and primary pain endpoint, trial B was intentionally over powered to 97%. There was no significant sequence or segment effect in any pain measure in either trial A or trial B. Results from the sensitivity analyses were consistent with the primary analgesic analyses.

Safety and Tolerability

Adverse Events. One subject in trial A discontinued due to AEs after administration of desmetramadol in the first segment. No subjects discontinued from trial B due to AEs.

After dosing with tramadol and desmetramadol in trial A, subjects reported a similar qualitative and quantitative profile of drug-related AEs (Table 12) (i.e., AEs for desmetramadol fell within the definition of "safe"). AEs were reported in 49% and 44% of subjects after tramadol and desmetramadol, respectively, compared with 24% of subjects after placebo. The five most common drug-related AEs after desmetramadol and tramadol in trial A were nausea, dizziness, headache, somnolence and pruritus. The severity of drug-related AEs in trial A were all grade 1 except for a single subject who reported grade 2 headache and dizziness after tramadol.

Drug-related AEs were reported in 27%, 50% and 67% of subjects in trial B after placebo, tramadol and desmetramadol, respectively (Table 12). Compared to the desmetramadol AE profile in trial B, the tramadol AE profile in the same subjects surprisingly featured less nausea (−50%), somnolence (−60%), headache (−40%), vomiting (−78%), presyncope (−83%) and pruritus (−75%). The tramadol AE profile in trial B surprisingly and unexpectedly resembled placebo except for an increased incidence of dizziness (8-fold placebo) and muscle spasticity (absent from placebo). Without wishing to be bound by theory, this is consistent with (+)-M1 mediating these AEs. The incidence of muscle spasticity after tramadol was the same as after desmetramadol.

TABLE 12

Summary of Drug-Related AEs (Safety Population)

| EVENT, | | TRIAL A (N = 43; M = 43) | | | TRIAL B (N = 60; M = 42, F = 18) | | |
|---|---|---|---|---|---|---|---|
| N (%) | | PLACEBO | TRAMADOL | DESMETRAMADOL | PLACEBO | TRAMADOL | DESMETRAMADOL |
| All AEs Specified AEs[†] | | 10 (24) | 20 (49) | 19 (44) | 16 (27) | 30 (50) | 40 (67) |
| Nausea | | 3 (7) | 5 (12) | 8 (19) | 7 (12) | 8 (13) | 16 (27) |
| | M | 3 (7) | 5 (12) | 8 (19) | 4 (10) | 6 (14) | 11 (26) |
| | F | — | — | — | 3 (17) | 2 (11) | 5 (28) |
| Dizziness | | 1 (2) | 5 (12) | 6 (14) | 1 (2) | 8 (13) | 12 (20) |
| | M | 1 (2) | 5 (12) | 6 (14) | 1 (2) | 4 (10) | 7 (17) |
| | F | — | — | — | 0 (0) | 4 (22) | 5 (28) |
| Somnolence | | 0 (0) | 2 (5) | 3 (7) | 2 (3) | 4 (7) | 10 (17) |
| | M | 0 (0) | 2 (5) | 3 (7) | 1 (2) | 2 (5) | 4 (10) |
| | F | — | — | — | 1 (6) | 2 (11) | 6 (33) |
| Headache | | 0 (0) | 7 (17) | 3 (7) | 3 (5) | 6 (10) | 10 (17) |
| | M | 0 (0) | 7 (17) | 3 (7) | 0 (0) | 0 (0) | 4 (10) |
| | F | — | — | — | 3 (17) | 6 (33) | 6 (33) |
| Vomiting | | 0 (0) | 1 (2) | 1 (2) | 1 (2) | 2 (3) | 9 (15) |
| | M | 0 (0) | 1 (2) | 1 (2) | 1 (2) | 2 (5) | 6 (14) |
| | F | — | — | — | 0 (0) | 0 (0) | 3 (17) |
| Presyncope | | | 0 (0) | 0 (0) | 0 (0) | 1 (2) | 6 (10) |
| | M | 1 (2) | 0 (0) | 0 (0) | 0 (0) | 1 (2) | 3 (7) |
| | F | — | — | — | 0 (0) | 0 (0) | 3 (17) |
| Pruritus | | 0 (0) | 4 (10) | 3 (7) | 1 (2) | 1 (2) | 4 (7) |
| | M | 0 (0) | 4 (10) | 3 (7) | 0 (0) | 0 (0) | 1 (2) |
| | F | — | — | — | 1 (6) | 1 (6) | 3 (17) |
| Spasticity | | 0 (0) | 1 (2) | 0 (0) | 0 (0) | 3 (5) | 3 (5) |
| | M | 0 (0) | 1 (2) | 0 (0) | 0 (0) | 3 (7) | 3 (7) |
| | F | — | — | — | 0 (0) | 0 (0) | 0 (0) |
| Feel abnormal | | 0 (0) | 1 (2) | 0 (0) | 0 (0) | 2 (3) | 3 (5) |
| | M | 0 (0) | 1 (2) | 0 (0) | 0 (0) | 2 (5) | 2 (5) |
| | F | — | — | — | 0 (0) | 0 (0) | 1 (6) |
| Feel hot | | 0 (0) | 0 (0) | 0 (0) | 1 (2) | 0 (0) | 3 (5) |
| | M | 0 (0) | 0 (0) | 0 (0) | 1 (2) | 0 (0) | 2 (5) |
| | F | — | — | — | 0 (0) | 0 (0) | 1 (6) |
| Euphoria | | 0 (0) | 0 (0) | 0 (0) | 0 (0) | 1 (2) | 2 (3) |
| | M | 0 (0) | 0 (0) | 0 (0) | 0 (0) | 1 (2) | 1 (2) |
| | F | — | — | — | 0 (0) | 0 (0) | 1 (6) |
| Sweating | | 0 (0) | 0 (0) | 0 (0) | 1 (2) | 1 (2) | 2 (3) |
| | M | 0 (0) | 0 (0) | 0 (0) | 1 (2) | 1 (2) | 2 (5) |
| | F | — | — | — | 0 (0) | 0 (0) | 0 (0) |
| Severe AEs | | 0 (0) | 0 (0) | 0 (0) | 0 (0) | 0 (0) | 0 (0) |
| Deaths | | 0 (0) | 0 (0) | 0 (0) | 0 (0) | 0 (0) | 0 (0) |

Abbreviations: M, male; F, female.
[†]AE incidence ≥ 3% of subjects dosed with desmetramadol in trial B.

Female subjects in trial B made up 30% of the safety population and 43% of the specified AEs. Drug-related AE severity in trial B was all grade 1 except for five subjects who had grade 2 drug-related AEs after placebo (somnolence), tramadol (asthenia) and desmetramadol (nausea/vomiting, feeling hot, hypotension). No deaths or serious AEs were reported in either trial A or trial B.

Respiration and Other Vital Signs. Respiration was assessed 1,744 times in trial A and 2,510 times in trial B. In trial A, respiratory rate was assessed before and after each of the nine study drug doses in each of the three treatment segments. Desmetramadol and tramadol had no discernable pre-dose versus post-dose effect on respiratory rate compared to placebo or compared to each other. Compared to baseline screening assessments in trial A, there was no effect of placebo, tramadol or desmetramadol on systolic/diastolic blood pressure, pulse and respiration at the end of each treatment segment. Paired comparisons of respiration were made between tramadol and placebo, desmetramadol and placebo, and desmetramadol and tramadol with respect to the average post-dose respiration. Average respiration after tramadol and desmetramadol were minimally reduced compared to placebo, and this reduction was statistically significant in the presence of paroxetine, but not in its absence (trial B mean paired difference [SD]=−0.34 [0.99] and −0.30 [0.90] breaths per minute; P=0.004 and P=0.012, respectively). There was no significant difference in respiration between desmetramadol and tramadol.

Discussion of Key Findings and Clinical Significance. Desmetramadol provided superior analgesia to tramadol in metabolically deficient subjects, the same group in which tramadol efficacy was lost. Surprisingly and unexpectedly, desmetramadol by itself provided the same qualitative and quantitative safety and efficacy profile as tramadol in metabolically sufficient subjects (i.e. intermediate and normal metabolizers with an activity score of 1.0 to 2.0), and the same as described in the FDA-approved tramadol label. This was surprising and unexpected because the enantiomers of tramadol are reported to have analgesic pharmacology of their own, with (+)-tramadol having μ-opioid receptor binding affinity ($K_i$ of 1.3 μM), (+)-tramadol inhibiting serotonin uptake ($K_i$ of 0.5 μM) and (−)-tramadol inhibiting norepinephrine uptake ($K_i$ of 0.5-1.6 μM) (Driessen, 1993, *Br J Pharmacol*, 108:806-11; Raffa 2012). At steady-state, both tramadol enantiomers reached about 0.5 μM mean concentration in the plasma of subjects. The ULTRAM® and ULTRACET® labels state that, "the relative contribution of both tramadol and M1 to human analgesia is dependent upon the plasma concentrations of each compound."

This tramadol-equivalent safety and analgesic efficacy of desmetramadol in metabolically sufficient subjects was also surprisingly and unexpectedly observed in subjects who were ultra-rapid metabolizers or metabolically deficient (i.e., deficient by genetics as a 'poor metabolizer' or an intermediate metabolizer with an activity score of 0.5, or deficient by inhibition of CYP2D6, such as with paroxetine). Desmetramadol thus obviates the metabolic liabilities of tramadol while preserving its safety profile, because it does not rely on the activity of CYP enzymes for its activity. This property of desmetramadol is significant because tramadol is widely used globally with 41 million prescriptions dispensed in 2017 in the United States alone, and an estimated third to nearly half of patients treated with tramadol fail to metabolize it to its active metabolite with optimal kinetics. This is the first human study to ask whether the tramadol parent enantiomers are essential for tramadol analgesia, or whether (−)-M1 and (+)-M1 alone can provide analgesia in the absence of tramadol. This study examined whether M1 is not only necessary, but sufficient to replicate tramadol analgesia in metabolically normal and intermediate subjects. Surprisingly and unexpectedly, the results showed that desmetramadol is sufficient to replicate the analgesic and safety profile of tramadol. Accordingly, desmetramadol is an effective substitute for tramadol's approved indications, i.e., for (a) the management of moderate to moderately severe pain in adults, and (b) the management of pain in adults that is severe enough to require an opioid analgesic and for which alternative treatments are inadequate. The findings also underscore that desmetramadol is also suitable for pain treatment where tramadol is now contraindicated for its safety liabilities in ultra-rapid metabolizers: that is, in the pediatric population.

In trial A, 50 mg tramadol and 20 mg desmetramadol dosed every 6 hours gave systemic (+)-M1 levels that were bioequivalent and (−)-M1 levels there were nearly statistically bioequivalent. In the absence of circulating tramadol enantiomers, desmetramadol produced similar responses as tramadol with respect to analgesia, pupil constriction, abuse measures, AE profile and vital signs. If tramadol enantiomers contributed to analgesia as dogma teaches, subjects should have experienced greater analgesia after tramadol, but surprisingly, they did not. Without being bound to any theory, the most straightforward interpretation of these findings is that circulating M1 enantiomers as provided by desmetramadol are not only necessary, but surprisingly are sufficient to replicate the therapeutic pharmacology of tramadol, both qualitatively and quantitatively. In this interpretation, tramadol provides superfluous enantiomers with (+)-tramadol contributing unwanted metabolic liabilities related to the under or over production of the (+)-M1 opioid, and unwanted serotonergic activity that may negatively influence analgesia and potentially contribute to the risk of seizure and serotonin syndrome.

The doses of tramadol and desmetramadol in trial A were advanced into trial B, where subjects were made metabolically deficient by co-administration of paroxetine, a strong inhibitor of CYP2D6 and CYP2B6. The presence of paroxetine in trial B depressed tramadol plasma (+)-M1 by ~60% and increased desmetramadol plasma (+)-M1 by ~40%. The effect of paroxetine on (−)-M1 levels was less pronounced, with tramadol plasma (−)-M1 decreased and desmetramadol plasma (−)-M1 increased by approximately the same amount. The net paroxetine effect in trial B caused tramadol and desmetramadol (−)-M1 to assume bioequivalent levels, and for tramadol (+)-M1 to be depressed to less than a third of the desmetramadol (+)-M1 level. Surprisingly, (−)-tramadol and (+)-tramadol levels in trial B rose to 200% of their levels in trial A in the absence of paroxetine. Despite the elevated levels of tramadol enantiomers and bioequivalent (−)-M1, the depression of (+)-M1 in trial B was surprisingly sufficient to cause the analgesic activity of tramadol to collapse to that of placebo. The finding underscores the surprisingly absent role tramadol enantiomers apparently play in mediating analgesia, since even elevated levels could not compensate for the loss of (+)-M1. In contrast, desmetramadol had no corresponding metabolic liability; in metabolically deficient subjects of trial B it produced therapeutic levels of both M1 enantiomers and analgesia as effective as in the metabolically unselected subjects of trial A. Desmetramadol also normalized the abnormal levels of tramadol M1 seen in genetic poor metabolizers and ultra-rapid metabolizers. As seen in trial A, desmetramadol returned M1 to therapeutic levels in a poor metabolizer and reduced M1 exposure in an ultra-rapid metabolizer. Accordingly, desmetramadol is an effective substitute for tramadol's approved indications in all CYP2D6 metabolizer phenotypes, i.e., in poor metabolizers, intermediate metabolizers, normal metabolizers, and ultra-rapid metabolizers, desmetramadol in the absence of tramadol can be used for (a) the management of moderate to moderately severe pain in adults, and (b) the management of pain in adults that is severe enough to require an opioid analgesic and for which alternative treatments are inadequate.

For prescribers seeking to lower the morphine milligram equivalents in their patients who require effective analgesia, tramadol is a viable option to the schedule II opioids that are central in the Opioid Crisis. Tramadol provides analgesia for moderate to moderately severe pain but compared to the schedule II opioids has a lower abuse potential and a substantially wider margin of safety with respect to respiratory depression and lethality in overdose. Critical shortcomings of tramadol relate to its metabolic liabilities. The findings from this study indicate that desmetramadol offers the safety and analgesia of tramadol but without its metabolic liabilities and CYP-mediated drug-drug interactions. Desmetramadol therefore offers expanded safety and utility for clinicians who already prescribe tramadol and as a new alternative to schedule II opioids.

While this invention has been particularly shown and described with reference to preferred embodiments thereof, it will be understood by those skilled in the art that various changes in form and details may be made therein without departing from the scope of the invention encompassed by the appended claims.

What is claimed is:

1. A method of treatment, comprising administering a pharmaceutical composition comprising desmetramadol, or a pharmaceutically acceptable salt thereof, in a dosage form that is substantially free of tramadol, to a human subject suffering from (a) moderate to moderately severe pain, or (b) pain that is severe enough to require an opioid analgesic and for which alternative treatments are inadequate, wherein the desmetramadol is a combination of (1R,2R)-desmetramadol and (1S,2S)-desmetramadol.

2. The method of claim 1, wherein the human subject is a poor metabolizer of tramadol, an intermediate metabolizer of tramadol, a normal metabolizer of tramadol, or an ultra-rapid metabolizer of tramadol.

3. The method of claim 1, further comprising a step of determining that the human subject is a poor metabolizer of tramadol, an intermediate metabolizer of tramadol, a normal metabolizer of tramadol, or an ultra-rapid metabolizer of tramadol.

4. The method of claim 3, wherein the CYP2D6 genotype of the human subject is measured.

5. The method of claim 1, further comprising a step of administering an inhibitor of CYP2D6 and/or CYP2B6.

6. The method of claim 1, further comprising a step of administering acetaminophen or ibuprofen.

7. The method of claim 6, wherein the pharmaceutical composition further comprises acetaminophen or ibuprofen.

8. The method of claim 1, further comprising a step of measuring pain or a change in pain.

9. The method of claim 8, wherein the pain is 5 or greater and the change in pain is 0.5 or more, each on a 10 cm visual analog scale, or 10-point verbal scale.

10. The method of claim 1, wherein the pharmaceutical composition comprises an amount of desmetramadol selected from the group consisting of 10, 20, 30, 40, 50, 60, 70, 80, 90, 100, 110, and 120 mg.

11. The method of claim 1, wherein the pharmaceutical composition comprises 10 to 30 mg desmetramadol and is administered every 4-6 hours.

12. The method of claim 1, wherein the pharmaceutical composition comprises 30 to 50 mg desmetramadol and is administered every 6-8 hours.

13. The method of claim 1, wherein the pharmaceutical composition comprises 40 to 60 mg desmetramadol and is administered every 8-10 hours.

14. The method of claim 1, wherein the pharmaceutical composition comprises 60 to 80 mg desmetramadol and is administered every 10-12 hours.

15. The method of claim 1, wherein the pharmaceutical composition comprises 80 to 120 mg desmetramadol and is administered every 20-24 hours.

16. The method of claim 1, wherein the pain is selected from the group consisting of acute pain, chronic pain and neuropathic pain.

17. The method of claim 1, wherein the pharmaceutically acceptable salt is desmetramadol hydrochloride.

18. The method of claim 1, wherein the pharmaceutical composition further comprises one or more pharmaceutical excipients selected from the group consisting of polysaccharide, acrylic resin, polyalkylene glycol, polyalkylene oxide, polyvinyl acetate, polyvinylpyrrolidone, protein-derived materials, colloidal silica, and mixtures thereof, wherein the pharmaceutical excipients are 10-95 wt. % of the pharmaceutical composition.

19. The method of claim 18, wherein the pharmaceutical composition further comprises one or more pharmaceutical excipients selected from the group consisting of microcrystalline cellulose, salts, and magnesium stearate.

20. The method of claim 18, wherein the pharmaceutical composition comprises 5-40 wt. % desmetramadol, or a pharmaceutically acceptable salt thereof.

21. The method of claim 18, wherein the polysaccharide consists of polysaccharide gums or cellulose ethers.

22. The method of claim 18, wherein the cellulose ether consists of hydroxyalkyl celluloses, carboxyalkyl celluloses, or mixtures thereof.

23. The method of claim 18, wherein the cellulose ether consists of hydroxyethyl celluloses, hydroxypropyl celluloses, hydroxypropylmethyl celluloses, carboxymethyl celluloses, or mixtures thereof.

24. The method of claim 18, wherein the acrylic resin consists of polymers or copolymers of acrylic acid, methacrylic acid, methyl acrylate, methyl methacrylate, or mixtures thereof.

25. The method of claim 1, wherein the human subject is a child younger than 12 years of age or a child younger than 18 years of age who has undergone a tonsillectomy and/or adenoidectomy.

26. The method of claim 1, wherein the in vitro dissolution of desmetramadol from the pharmaceutical composition has a difference factor (f1) of 0 to 15 or a similarity factor (f2) of 50 to 100 for desmetramadol release, wherein the f1 and f2 reference values are 34% desmetramadol released at 1 hour, 50% desmetramadol released at 2 hours, 62% desmetramadol released at 3 hours, 71% desmetramadol released at 4 hours, 85% desmetramadol released at 6 hours, and 93% desmetramadol released at 8 hours.

27. The method of claim 26, wherein the in vitro dissolution is measured using a USP Apparatus I Basket Method at 75 rpm in a buffer.

28. The method of claim 27, wherein the buffer has a pH selected from 1.2, 4.5, 6.8 and 7.4.

29. The method of claim 1, wherein the dosage form is for parenteral administration.

* * * * *